(12) United States Patent  (10) Patent No.: US 7,883,535 B2
Cantin et al.  (45) Date of Patent: Feb. 8, 2011

(54) DEVICE AND METHOD FOR TRANSMITTING MULTIPLE OPTICALLY-ENCODED STIMULATION SIGNALS TO MULTIPLE CELL LOCATIONS

(75) Inventors: Daniel Cantin, Sainte-Foy (CA); Alain Cournoyer, Québec (CA); Pierre Galarneau, Cap-Rouge (CA); Chiara Meneghini, Vicenza (IT)

(73) Assignee: Institut National D'Optique, Quebec, Quebec (CA)

( * ) Notice: Subject to any disclaimer, the term of this patent is extended or adjusted under 35 U.S.C. 154(b) by 1244 days.

(21) Appl. No.: 11/271,210

(22) Filed: Nov. 9, 2005

(65) Prior Publication Data

US 2006/0129210 A1    Jun. 15, 2006

Related U.S. Application Data

(60) Provisional application No. 60/625,977, filed on Nov. 9, 2004.

(51) Int. Cl.
*A61N 5/06* (2006.01)
(52) U.S. Cl. .............................. 607/89; 607/88; 128/898
(58) Field of Classification Search ................... 607/88, 607/89; 128/898
See application file for complete search history.

(56) References Cited

U.S. PATENT DOCUMENTS

| | | | |
|---|---|---|---|
| 3,900,034 A | 8/1975 | Katz et al. | |
| 4,279,256 A | 7/1981 | Bucalo | |
| 4,640,286 A | 2/1987 | Thomson | |
| 4,740,047 A | 4/1988 | Abe et al. | |
| 4,819,632 A | 4/1989 | Davies | |
| 4,848,999 A * | 7/1989 | Taylor | 65/407 |
| 5,253,312 A | 10/1993 | Payne et al. | |
| 5,428,699 A | 6/1995 | Pon | |
| 5,445,608 A | 8/1995 | Chen et al. | |
| 5,505,726 A | 4/1996 | Meserol | |
| 5,586,982 A | 12/1996 | Abela | |
| 5,665,706 A | 9/1997 | DaVanzo et al. | |
| 5,772,657 A | 6/1998 | Hmelar et al. | |
| 5,832,931 A | 11/1998 | Wachter et al. | |
| 5,851,225 A | 12/1998 | Lawandy | |
| 5,955,624 A | 9/1999 | Nudelman et al. | |
| 5,962,434 A | 10/1999 | Schnaar et al. | |
| 5,968,905 A | 10/1999 | Patterson | |
| 6,042,603 A | 3/2000 | Fisher et al. | |
| 6,099,864 A | 8/2000 | Morrison et al. | |
| 6,120,460 A | 9/2000 | Abreu | |

(Continued)

OTHER PUBLICATIONS

Loizou, Philipos C., "Mimicking the human ear", IEEE Signal Processing Magazine, Sep. 1998, pp. 101-130.

(Continued)

*Primary Examiner*—Henry M Johnson, III
*Assistant Examiner*—Jeffery B Lipitz
(74) *Attorney, Agent, or Firm*—Merchant & Gould P.C.

(57) ABSTRACT

The present invention concerns a device and method for transmitting multiple optically-encoded stimulation signals to multiple stimulation sites, especially cell locations. The device uses a primary optical fiber to transmit specific wavelength components of an encoded light signal to output positions along the fiber where they are coupled out of the primary fiber to stimulation sites via electrodes for electrical stimulation of the sites or optical windows and/or secondary optical fibers for photo-stimulation of sites.

65 Claims, 16 Drawing Sheets

U.S. PATENT DOCUMENTS

| | | | |
|---|---|---|---|
| 6,159,196 | A | 12/2000 | Ruiz |
| 6,233,480 | B1 | 5/2001 | Hochman et al. |
| 6,242,258 | B1 | 6/2001 | Haselton, III et al. |
| 6,259,841 | B1* | 7/2001 | Bhagavatula ................. 385/47 |
| 6,310,083 | B1 | 10/2001 | Kao et al. |
| 6,372,183 | B1 | 4/2002 | Akong et al. |
| 6,379,955 | B1 | 4/2002 | Kopelman et al. |
| 6,400,487 | B1 | 6/2002 | Harris et al. |
| 6,436,129 | B1 | 8/2002 | Sharkey et al. |
| 6,458,157 | B1 | 10/2002 | Suaning |
| 6,505,075 | B1 | 1/2003 | Weiner |
| 6,510,338 | B1 | 1/2003 | Irion et al. |
| 6,510,347 | B2 | 1/2003 | Borkan |
| 6,640,121 | B1 | 10/2003 | Telischi et al. |
| 6,662,039 | B2 | 12/2003 | Yuste et al. |
| 6,668,190 | B2 | 12/2003 | Iezzi et al. |
| 6,721,603 | B2 | 4/2004 | Zabara et al. |
| 6,743,581 | B1 | 6/2004 | Vo-Dinh |
| 6,896,870 | B1 | 5/2005 | Mazar et al. |
| 7,395,118 | B2* | 7/2008 | Erickson ..................... 607/116 |
| 2002/0010500 | A1* | 1/2002 | Chen ........................... 607/89 |
| 2002/0042638 | A1* | 4/2002 | Iezzi et al. ..................... 607/88 |
| 2002/0051806 | A1 | 5/2002 | Mallapragada et al. |
| 2002/0156349 | A1* | 10/2002 | Yamaki et al. ............... 600/178 |
| 2003/0036855 | A1 | 2/2003 | Harris et al. |
| 2003/0040080 | A1 | 2/2003 | Miesenbock et al. |
| 2003/0090756 | A1* | 5/2003 | Moon et al. .................. 359/110 |
| 2003/0161817 | A1 | 8/2003 | Young et al. |
| 2003/0231818 | A1 | 12/2003 | Cantin et al. |
| 2004/0015211 | A1* | 1/2004 | Nurmikko et al. ............. 607/61 |
| 2004/0088015 | A1 | 5/2004 | Casavant et al. |
| 2004/0107453 | A1 | 6/2004 | Furcht et al. |
| 2004/0152192 | A1 | 8/2004 | Bachovchin et al. |
| 2004/0166553 | A1 | 8/2004 | Nguyen et al. |
| 2004/0172100 | A1 | 9/2004 | Humayun et al. |
| 2004/0234455 | A1 | 11/2004 | Szalay |
| 2004/0266003 | A1 | 12/2004 | Powell et al. |
| 2005/0042662 | A1 | 2/2005 | Li et al. |
| 2005/0059028 | A1 | 3/2005 | Nguyen et al. |
| 2005/0069878 | A1 | 3/2005 | Yue et al. |
| 2005/0070987 | A1* | 3/2005 | Erickson ..................... 607/122 |
| 2005/0203601 | A1 | 9/2005 | Palanker et al. |
| 2005/0216072 | A1 | 9/2005 | Mahadevan-Jansen et al. |
| 2005/0234529 | A1* | 10/2005 | Oghalai et al. ................. 607/89 |
| 2005/0240229 | A1* | 10/2005 | Whitehurst et al. ............. 607/2 |
| 2006/0107744 | A1* | 5/2006 | Li et al. ......................... 73/657 |
| 2009/0163982 | A1* | 6/2009 | deCharms .................... 607/89 |

OTHER PUBLICATIONS

Zheng, James Q., "Turning of nerve growth cones induced by localized increases in intracellular calcium ions", Nature, Jan. 6, 2000, vol. 403, pp. 89-93.
Cooper-Capps, Vivian, "Stimulating nerve cells with laser precision", Exploration: Online Research Journal of Vanderbilt University, Mar. 10, 2005.
Boucsein, Clemens et al., "Controlling synaptic input paterns in vitro by dynamic photo stimulation", Journal of Neurophysiology, May 2005, vol. 94, pp. 2948-2958.
Hoffer, Andy, "NeuroStream Technologies Inc.", The Centre for Systems Science: Update Newsletter, vol. 13, Issue 3, Nov. 2001, website: css.sfu.ca/update/vol13/13.3.neurostream.html.
"New neurons can get out of spinal cord", Science Blog, Topic: Bio and Medicin, Date: Friday, Apr. 30 @ 12:00:00 CDT, website: www.scienceblog.com/community/article-print-2683.html.
Richter, C.-P. et al., "Optically-evoked acoustic nerve activity", Northwestern University, Chicago, Illinois, 1-page poster presentation #1012.
Izzo, A.D. et al., "Safe ranges for optical cochlear neuron stimulation", Northwestern University, Chicago, Illinois, 1-page poster presentation #1013.
Lamonta, Nancy D., "Artificial synapse chip could act as a retinal prosthesis", Biophotonics International, Sep. 2004, vol. 11, No. 9, Laurin Publication, pp. 23-24.
Sershen, S. R. et al., "Nanoshell-polymer composites for photothermally modulated drug delivery", Conference in Lasers and Electro-Optics (CLEO): presentation, Baltimore, MD, May 2001.
Nie, Shuming, "QDs simultaneously target and image tumors in vivo", Micro/Nano, p. 10; work is also described in the Aug. 1, 2004 issue of the journal Nature.
"Light-activated complex kills virus", Biophotonics International, Sep. 2004, vol. 11, No. 9, Laurin Publication, p. 14.
Lerner, Eric J., "Light-emitting antennas through nano-optics", Optics & Photonics News, Sep. 2005, p. 6.
Chase, Victor D., "Mind over muscles", Technology Review, Mar./Apr. 2000, pp. 38-45.
Boyden, Edward S. et al., "Millisecond-timescale, genetically targeted optical control of neural activity", Nature Neuroscience, Sep. 2005, vol. 8, No. 9, pp. 1263-1268.
Pogue, Brian W. et al., "Targeting in photodynamic therapy and photo-imaging", Optics & Photonics News, Aug. 2003, pp. 36-43.
Chiou, Arthur E., "Harnessing light for life: An overview of biophotonics", Optics & Photonics News, Sep. 2005, pp. 30-35.
Ohtsu, Motoichi (ed.), Progress in Nano-Electro-Optics II (Novels Devices and Atom Manipulation), 2004, Springer-Verlag, 190 p., ISBN: 3-540-05042-6; -Review by Daniela Dragoman in Optics & Photonics News, Sep. 2005, vol. 16, No. 9, p. 40.
"Hairlike percutaneous photochemical sensors", Nasatech Briefs, Apr. 2004, NASA's Jet Propulsion Laboratory, Pasadena California, website: www.nasatech.com/Briefs/Apr04/NPO30651.html; work done by Thomas George of Caltech and Gerald Loeb of the University of Southern California for NASA's Jet Propulsion Laboratory.
Brody, Tjhomas B., "The interactive fly: Genes involved in tissue and organ development", Weizmann Institute of Science, Israel, website: bioinformatics.weizmann.ac.il/databases/flybase/allied-data/interactive-fly/aimorph/brain4.html;email: brodyt@codon.nih.gov.
Wickramanayake, Wasala M.S. et al., "Controlled photo stimulation of neuron cells and activation of calcium ions on semiconductor quantum dot layer-by-layer assemblies", The 2005 Annual Meeting: conference presentation, Nov. 1, 2005-2:30 pm, website: aiche.confex.com/aiche/2005/techprogram/P23470.HTM.
Sawan, Mohamad, "Wireless smart implants dedicated to multichannel monitoring and microstimulation", ICPS, 2004, pp. 21-26, 2004 IEEE/ACS International Conference on Pervasive Services (ICPS'04), Jul. 19-23, 2004, American University of Beirut (AUB), Lebanon, invited paper. website: http://136.199.54.185/~ley/db/conf/icps/icps2004.html; icps2004.cse.ogi.edu/talks/Sawan-ICPS.pdf.
Litvak, L.M. et al., "Auditory nerve fiber responses to electric stimulation: modulated and unmodulated pulse trains", preliminary draft of article in Journal of the Acoustical Society of America, Jul. 2001, vol. 110, No. 1, pp. 368-379.
Rosahl, Steffen K. et al., "Far-field responses to stimulation of the cochlear nucleus by microsurgically placed penetrating and surfaces electrodes in the cat", Neurosurg Focus Preview for J. Neurosurg, vol. 95, Nov. 2001, pp. 845-852.
Greenberg, Robert J. et al., "A computational model of electrical stimulation of the retinal ganglion cell", IEEE transactions on Biomedical Engineering, vol. 46, No. 5, May 1999, pp. 505-514.
Zheng, James Q., Research Overview, Neurobiology Laboratory, Robert W. Johnson Medical School, Piscataway NJ; website: www2.umdnj.edu/zhlabweb/overview.htm.
U.S. Appl. No. 11/254,802, Beaulieu et al.
Öberg, P. Åke et al. (eds.), Sensors in Medicine and Health Care. Sensors Applications, May 2004, pp. 309-338, vol. 3, Wiley-VCH Verlag GmbH & Co. KGaA, Weinheim.
"NIDCD—funded Research Explores Use of Laser to Stimulate Auditory Nerve." NEWS- Northwestern University: McCormick School of Engineering, McCormick News Article, Jan. 10, 2007 (http://www.mccormick.northwestern.edu/news/article.php?id=269).
Infrared Nerve Stimulation, Aculight Corporation, webpage http://www.aculight.com/infrarednervestimulator.html.

Renoir Model R-1850 Infrared Stimulator, Aculight Corporation, webpage http://www.aculight.com/Downloads/Infrared%20Nerve%20Stimulator10.6.2006.pdf.

Izzo, Agnella D.; Walsh Jr., Joseph T.; Richter, Claus-Peter; and Jansen, E. Duco; Abstract No. 162 "Optical Stimulation of the Gerbil Cochlea: Characterization of Sensory Nervous System Stimulation in an in Vivo Animal Model", American Society for Laser Medicine and Surgery Abstracts—Published online in Wiley InterScience (www.interscience.com), DOI 10.1002/lsm.20167, p. 49.

Wells, Jonathan; Kao, Chris; Mariappan, Karthik; Albea, Jeffrey; Jansen, Duco E.; Konrad, Peter and Jansen-Mahadevan, Anita; "Optical stimulation of neural tissue in vivo", Optics Letters / vol. 30, No. 5 / Mar. 1, 2005, p. 504-506.

Wells, Jonathan; Kao, Chris; Jansen, Duco E.; Konrad, Peter and Mahadevan-Jansen, Anita; "Application of Infrared light for in vivo neural stimulation", Journal of Biomedical Optics 10(6), 064003 (Nov./Dec. 2005), p. 1-12.

* cited by examiner

DEVICE AND METHOD FOR TRANSMITTING MULTIPLE OPTICALLY-ENCODED STIMULATION SIGNALS TO MULTIPLE CELL LOCATIONS

FIELD OF THE INVENTION

The present invention relates generally to a device and method for stimulating cells. More specifically, the present invention relates to a device and method for transmitting multiple optically-encoded stimulation signals to multiple stimulation sites, especially cell locations.

BACKGROUND OF THE INVENTION

In various medical fields, the use of artificial stimulation devices, or prosthesis, to stimulate damaged cells and/or tissue which are no longer responsive to natural stimuli is well known. These devices mimic natural impulses and act to re-establish the natural stimulation path.

One of the best examples of the success of such an approach is the use of the cochlear implant to restore partial hearing in profoundly deaf people. A person is diagnosed as profoundly deaf if either a very large number of hair cells or auditory neurons throughout the cochlea, the spiral-shaped cavity of the inner ear, are damaged. Cochlear implants use electrical stimulation to directly excite the remaining auditory neurons which connect the ear to the brain. In general, such implants include a microphone which picks up sound, an array of electrodes surgically inserted into the cochlea, which electrically stimulates functional auditory neurons of the cochlea, and a signal transmission system which transmits the sound information from the microphone to the array of electrodes. The whole system is designed so that activation of the electrodes will fire up the neurons, which communicate with the patient's central nervous system, and thereby transmit information about the acoustic signal to the brain.

In practice, implementation of existing cochlear implant technology is impeded by the size of the wires used to transmit information to the neurons. The minimum diameter of such a wire being about 25 μm (P. Åke Öberg, Tatsuo Togawa, Francis A. Spelman (eds.), Sensors in Medicine and Health Care, Sensors Applications Volume 3, Wiley-VCH Verlag GmbH & Co. KGaA, 2004), the number of wires is limited to less than one hundred (100) by the diameter of the auditory canal. By increasing the number of electrodes, it is hoped that the resolution of the perceived acoustic signal can be improved. Moreover, by decreasing the diameter of the wire, the risk of injury to the cochlea and its inner structure, which includes the basilar membrane and the hair cells, is reduced. This risk of injury inherent with electrical charge is of import given the increase in popularity of cochlear implants and their growing consideration for use in patients with residual hearing. One other solution would be to develop a device which uses non-electrical artificial stimulation, for example optical or photo-stimulation. US Patent Application No. 2005/0216072 (MAHADEVAN-JANSEN) discloses a system and methods for optical stimulation of neural tissues. However, one major drawback with this system and these methods lies in the probe: the probe delivers optical energy to the target neural tissue, one site at a time and at a distance away from the target neural tissue.

Applications of electrical stimulation systems are not limited to cochlear implants. They include brain neuro-stimulation (pain relief, tremor control, treatment of cerebral palsy, treatment of Parkinson's disease, visual cortex implants for the blind), spinal neuro-stimulation (pain relief, peripheral vascular flow enhancement), peripheral nerve stimulation (pain relief, phrenic nerve pacing), retinal implants, heart pacemakers, tissue-growth stimulation and inhibition, etc.

Functional Electrical Stimulation (FES) is used to produce, by means of electrical stimulation, contractions in muscles either injured or paralysed due to central nervous system lesions. In the case of FES, arrays of electrodes are implanted under the skin and used to choreograph movement in the patient's muscles.

Applications for this approach are found, for example, in cases of stroke, spinal cord injury, head injury, cerebral palsy, and multiple sclerosis. Here, too, resolution is limited by the size of the wires used for electrical stimulation.

Efforts are underway to develop visual prostheses, both retinal and cortical. Retinal prostheses aim to restore some form of vision to patients that are blind owing to a degenerative condition, such as retinitis pigmentosa or age-related macular degeneration, by bypassing the photoreceptor cells of the retina which have become dysfunctional and electrically stimulating the relatively intact retinal ganglion cells which connect the eye to the visual cortex of the brain. Electrical stimulation of the retinal ganglion cells creates the sensation of a spot of light (or phosphene) in the spatial vicinity of the stimulation. Cortical prostheses may be used to treat patients with secondary blindness not due to retinal or optic nerve disease. The difficulty with cortical implants lies in the need for intracranial surgery and the complexity of brain geometry. Nevertheless, both types of prostheses are faced with the problems inherent with electrical stimulation: injury incurred by neurons under chronic use and lack of specificity. U.S. Pat. No. 6,458,157 (SUANING) discloses an apparatus in which all tissue-contacting components may be fabricated from materials known to be well tolerated by human tissue. While SUANING discloses attempts that have been made to limit injury due to long-term use, the matter of specificity is not expressly addressed.

In general, traditional methods and devices for direct electrical neuro-stimulation lack spatial, physiological and strength specificities. Furthermore, they are prone to electrical interference from the environment. For example, electrical stimulation of the visual cortex produces phosphenes (or blurred) spots rather than pixel-like (or well-defined) spots. Stimulating tactile sense through electrical stimulation of specific neuronal cells is practically impossible without stimulating muscles and/or a temperature response, producing hitching or pain. A stimulation device permitting stimulation of specific neural ganglion cells would allow for better control of the stimulation process.

While certain cell, tissue, or system functions can be affected or controlled through electrical stimulation, a more efficient means of regulating these functions would be through the use of natural biochemical stimulators or inhibitors that are target specific. For example, insulin is produced naturally by the pancreas and is used by the body to activate glucose metabolism. Insulin production cannot be induced through electrical stimulation. Diabetics, who count for more than 5% of North Americans, must inject themselves with insulin in order to metabolise the glucose present in their body. A more convenient means of regulating the level and production of insulin would greatly benefit diabetics. The same holds true for people that must take medications regularly either orally or through injection.

Recent developments in nanotechnology (nanoshells, quantum dots (QDs), micelles), photodynamic therapy and photo-imaging offer new possibilities for improving specificity. These new technologies provide ways to cage, tag and locate molecules thus allowing the regulation and monitoring of optical stimulation mechanisms. Of particular interest are molecular structures or compounds that undergo changes in their properties (chemical affinity, conformal structure or composition) upon exposure to light (photoactivated changes). Following photoactivation, these molecules can react with other molecules or cells or emit light. In some cases, molecules undergo photoactivation only in the presence of certain other molecules or cells thus allowing these photoactivated molecules to be used as targets for locating, monitoring, imaging or destroying these other molecules or cells when lighted. For example, U.S. Pat. No. 6,668,190 (IEZZI et al.) discloses a drug delivery system that includes a fluid channel for delivering a drug to one of a number of sites and a light channel for delivering light to an area near one of the sites for photoactivating caged and/or non-caged molecules of the drug to stimulate neurological tissue.

From all of the above, there is a need for an improved manner of delivering either electrical or optical stimulations to specific stimulation sites of any type.

SUMMARY OF THE INVENTION

It is an object of the present invention to propose a device that optically-encodes stimulation information and transmits this stimulation information to multiple stimulation sites.

In accordance with one aspect of the present invention, there is therefore provided a stimulation device for transmitting stimulation information to a plurality of stimulation sites. The device includes light generating means for generating light having a plurality of wavelength components, encoding means for separately encoding at least a portion of the stimulation information into each of the wavelength components, and a multiplexing arrangement for multiplexing the wavelength components encoded by the encoding means into an encoded light signal. The device further includes a primary waveguide having an input end operationally connected to the multiplexing arrangement for receiving the encoded light signal, a light-guiding axis for guiding the encoded light signal therealong and an output end adapted to be positioned proximate the stimulation sites. In addition to the above elements, the device also has outcoupling means provided at the output end of the primary waveguide. These outcoupling means transversally couple each of the wavelength components of the encoded light signal out of the primary waveguide at different output positions along the light-guiding axis, each of the output positions being coupled to one of the stimulation sites.

In one embodiment of the device, the device preferably includes a number of electrodes, each associated with one of the output positions, for transducing a corresponding wavelength component into an electrical stimulation signal.

In another embodiment of the device, the device preferably includes an optical window in the primary waveguide at each of the output positions, in order to output an optical stimulation signal therefrom.

In accordance with another aspect of the present invention, there is provided a method for transmitting stimulation information to a plurality of stimulation sites. The method includes the steps of:
  a) generating light having a plurality of wavelength components;
  b) separately encoding at least a portion of the stimulation information into each of these wavelength components;
  c) multiplexing the wavelength components encoded by the encoding means into an encoded light signal;
  d) guiding the encoded light signal along a light-guiding axis of a primary waveguide; and
  e) transversally coupling each of the wavelength components of the encoded light signal out of the primary waveguide at different output positions along the light-guiding axis, each of the output positions being coupled to one of the stimulation sites.

Preferably, the above method includes an additional step (f) of converting said wavelength components into electrical stimulation signals.

In yet another embodiment, the transversal coupling of step (e) includes outputting each of the wavelength components through an optical window provided in the primary waveguide at each of the output positions.

In accordance with one embodiment of the invention, there is also provided a cochlear implant for transmitting auditory stimulation information to auditory neurons of the cochlea in situ of a patient. The cochlear implant includes a light generating means for generating light having a number of wavelength components, an encoding means for separately encoding at least a portion of the auditory stimulation information into each of the wavelength components, and a multiplexing arrangement for multiplexing the wavelength components encoded by the encoding means into an encoded light signal. The cochlear implant further includes a primary waveguide having an input end operationally connected to the multiplexing arrangement for receiving the encoded light signal therefrom, a light-guiding axis for guiding the encoded light signal therealong and an output end adapted to be positioned proximate the auditory neuron sites of the cochlea. In addition to the above elements, the device also has outcoupling means provided at the output end of the primary waveguide. These outcoupling means transversally couple each of the wavelength components of the encoded light signal out of the primary waveguide at different output positions along the light-guiding axis, each of the output positions being coupled to one of the auditory neuron sites of the cochlea. In one embodiment, the cochlear implant preferably includes a number of electrodes, each associated with one of the output positions, for transducing a corresponding wavelength component into an electrical stimulation signal. In another embodiment, the cochlear implant preferably includes an optical window in the primary waveguide at each of the output positions, in order to output an optical stimulation signal therefrom.

Advantages of the present invention include enhanced transmission efficiency (no cross-talking) of optically multiplexed stimulation signals, enhanced resolution achieved through the smaller size of the surface area at the output position interface and the increased number of output position interfaces.

Certain embodiments of the invention exhibit additional advantages: reduced or eliminated risk of injury due to electrical charge (toxicity due to electrode breakdown and heat damage), a more painless stimulus, and targeted and timed delivery of treatment via photoactivation of biochemical compounds or cellular/tissue functions at stimulation sites.

BRIEF DESCRIPTION OF THE DRAWINGS

Further aspects and advantages of the invention will be better understood upon reading the description of preferred embodiments thereof with reference to the following drawings:

FIG. 6 is a schematic illustration of a variant of the assembly of FIG. 5.

FIG. 9 is a cross-sectional side view of the output end of a device according to another preferred embodiment of the invention, showing dielectric reflectors used to transversally couple different wavelength components of the encoded light signal out of the primary waveguide at different output positions along and around the light guiding axis.

DESCRIPTION OF PREFERRED EMBODIMENTS OF THE INVENTION

In the following description, the terms "optical fiber" and "fiber" are used in a general manner and include all types of optical waveguides. The term "light" is used to refer to all electromagnetic radiation, including visible light. Furthermore, the term "optical" is used to qualify all electromagnetic radiation, including light in the visible spectrum.

The present invention relates to a stimulation device for transmitting stimulation information to a number of stimulation sites. It is understood throughout the present application that the present device may be used for either the electrical or the optical stimulation of cells, molecules, etc, and that the expression "stimulation information" refers to any appropriate signal modulation accomplishing the required stimulation. The stimulation sites may be embodied by cell sites or any other location where stimulation is needed, either in vitro or in vivo.

Generally, the device according to the present invention provides for the encoding of the stimulation information into different wavelength components which are then multiplexed into an encoded light signal. The encoded light signal is coupled in the input end of a primary waveguide and guided therein along a light guiding axis. Preferably, the primary waveguide is a length of optical fiber. The primary waveguide has an output end adapted to be positioned proximate the stimulation sites. Each wavelength component is coupled out of the primary waveguide at different output positions along the light-guiding axis, each of the output positions being coupled to one of the stimulation sites. In this manner, independent stimulation signals may be sent simultaneously to different stimulation sites, improving the specificity of the stimulation process.

Various embodiments of components embodying the stimulation device according to preferred embodiments of the invention will be described with reference to the appended drawings.

Devices According to Preferred Embodiments of the Invention

Figure 1:
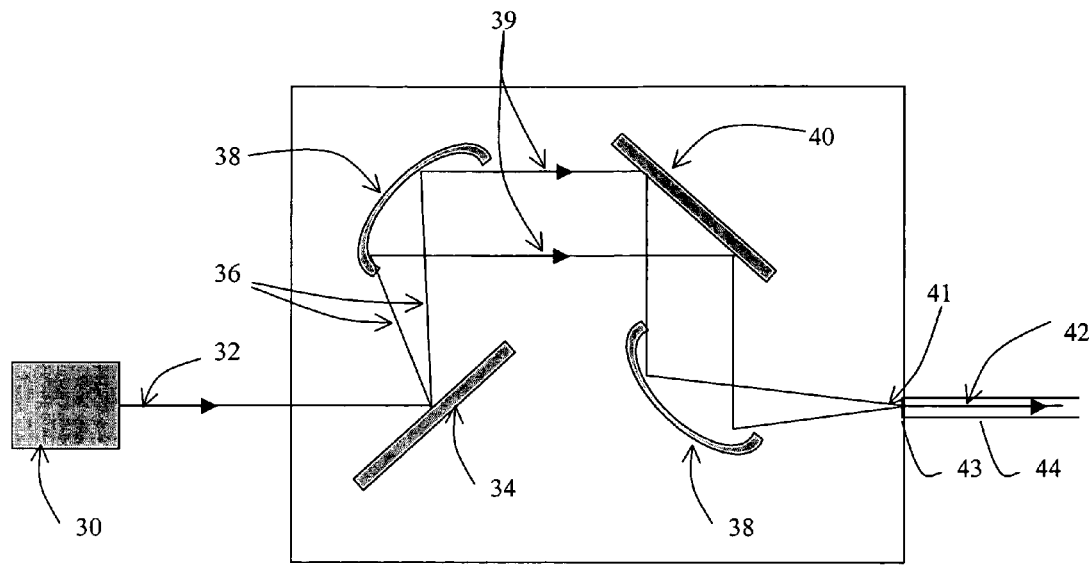
FIG. 1 is a schematic illustration of an assembly for generating a multiplexed multi-wavelength encoded light signal for a device according to a preferred embodiment of the invention.

The stimulation device according to the present invention first includes light generating means for generating light having a plurality of wavelength components. The light generating means may include a single monochromatic light source, such as a light-emitting diode or laser diode, or a number of such sources. Referring to FIG. 1, there is shown an embodiment of the invention where the light generating means are embodied by a single light source 30 generating a multi-wavelength light signal 32. The generated light 32 coming out of the source is collimated using standard collimation techniques adapted to the light source 30. The device further includes encoding means for encoding at least a portion of the stimulation information into individual wavelength components produced by the light source. The expression "wavelength component" is used herein to refer to either a single wavelength $\lambda$ or a finite wavelength band or channel $\Delta\lambda$. For convenience, the wavelength components will generally be designated by the symbol $\Delta\lambda$. In the embodiment of FIG. 1, the different wavelength components ($\Delta\lambda_1, \Delta\lambda_2, \ldots, \Delta\lambda_n$) of the multi-wavelength light signal 32 are first spatially separated by a dispersive element 34 and with the help of a focussing element 38, the separated wavelength components 36 are then redirected in a collimated beam 39. The signal amplitude of each different wavelength component ($\Delta\lambda_1, \Delta\lambda_2, \ldots, \Delta\lambda_n$) is then individually controlled with a spatial light modulator (SLM) 40. The spatial light modulator may for example be embodied by a liquid crystal display (LCD) linear array or a linear array of micro-mirrors. This control on the signal amplitude of each wavelength band ($\Delta\lambda_1, \Delta\lambda_2, \ldots, \Delta\lambda_n$) allows the encoding of a portion of the stimulation information into each of the separated wavelength components 36. Depending on the target application of the device, each wavelength component may be encoded with the same or different stimulation information as the other wavelength components.

The resulting collimated light beam with separated wavelength components 36 having different signal amplitudes along its transverse direction is then multiplexed into a unique encoded light signal 42 at the focal point 41 of another focusing element 38, preferably a cylindrical focussing element and enters the input end 43 of the primary optical fiber 44. As will be readily understood by one skilled in the art, any alternative optical component of the optical arrangement may be used in order to multiplex the encoded wavelength components together.

Of course, the multiplexed encoded light signal may be obtained by a variety of different appropriate optical assemblies. By way of example, FIGS. 2 to 6 and 6A show alternate manners of generating, encoding and multiplexing a plurality of wavelength components according to preferred embodiments of the present invention.

Figure 2:
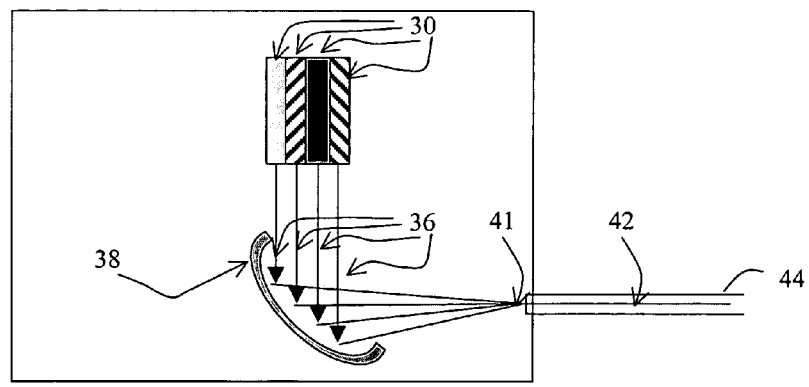
FIG. 2 is a schematic illustration of an assembly for generating a multiplexed multi-wavelength light signal, according to another preferred embodiment of the invention.

Referring to FIG. 2, there is shown an embodiment where different collimated sources 30 are used to generate a multi-wavelength encoded light signal 42. Each source 30 emits a collimated light beam 36 of a different spectral bandwidth $\Delta\lambda$ selected to embody one wavelength component. The emitted collimated light beam 36 is modulated at the source so as to encode the stimulation information therein. The collimated light beam 36 from each source 30 is then multiplexed using a focussing element 38, preferably a spherical mirror, into a unique encoded light signal 42 at the focal point 41 of the focusing element 38. This arrangement provides a more efficient means of coupling the encoded light signal 42 into the primary waveguide 44 by allowing focussing of the generated light beam 36 along both (vertical and horizontal) axes.

Figure 3:
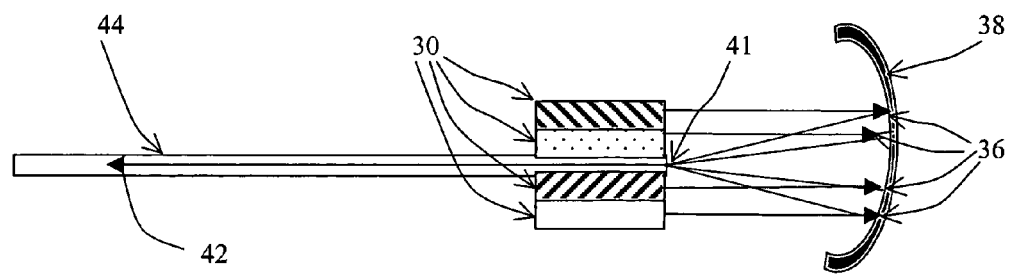
FIG. 3 is a schematic illustration of an assembly for generating a multiplexed multi-wavelength light signal, according to yet another preferred embodiment of the invention.
Figure 4:
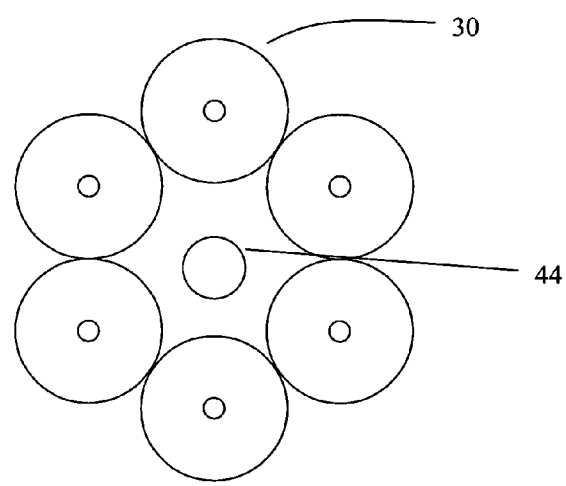
FIG. 4 is a front view illustration of the assembly of FIG. 3.

Yet another embodiment is shown in FIGS. 3 and 4. Similar to the embodiment of FIG. 2, different collimated sources 30 are used; each source emitting one wavelength component in the form of a collimated light beam 36 of a different spectral bandwidth $\Delta\lambda$ and each modulated to be encoded directly with the required stimulation information. Unlike the arrangement shown in FIG. 2, the sources 30 are arranged around the primary optical fiber 44. The collimated light beam 36 of each source is directed to a focussing element 38 that reflects it towards a focal point 41 proximate the input end of the primary optical fiber 44. The focussing element 38 is preferably a metallic-coated spherical mirror. The mirror coating is chosen to allow good reflectivity at all source wavelengths whereas its radius of curvature is such that the beams are all directed and focused to fit into the core of the primary waveguide 44 and the numerical aperture. The different collimated light beams 36 originating from the different sources 30 are multiplexed into a multi-wavelength encoded light signal 42 at this focal point 41 which is then coupled into the primary optical fiber 44. This scheme advantageously provides a more efficient coupling of the various light sources into the primary fiber over the one presented in FIG. 2 because the collimated light beams from the various light sources have similar optical paths.

Figure 5:
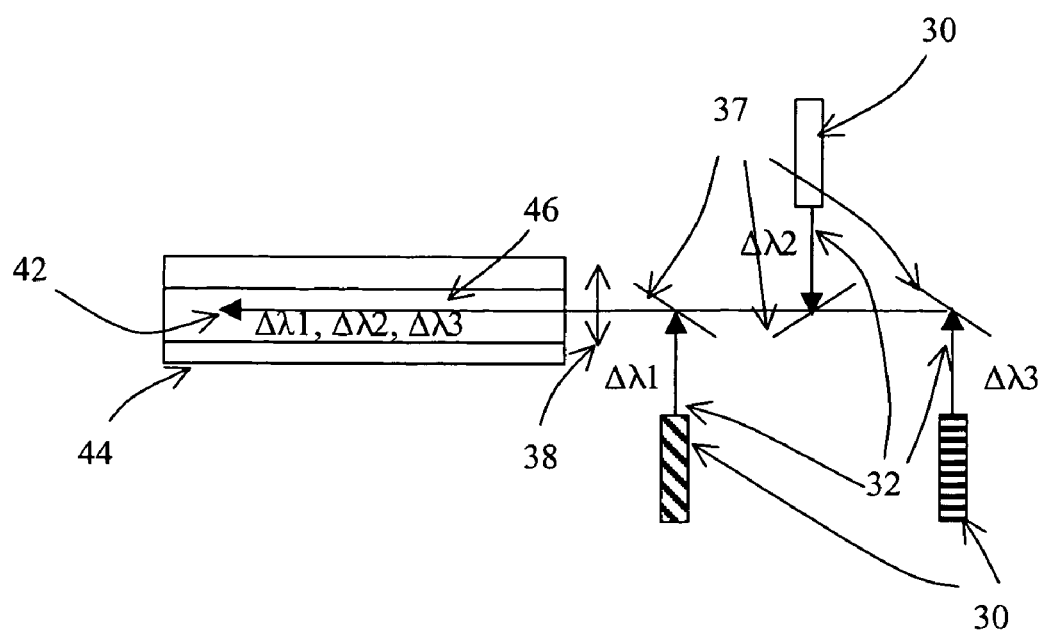
FIG. 5 is a schematic illustration of an assembly for generating a multiplexed multi-wavelength light signal showing the use therein of dichroic (or dielectric-coated) mirrors, according to yet another preferred embodiment of the invention.

Another possible arrangement for the generation of an encoded multiplexed multi-wavelength signal is provided in FIG. 5. Here different light sources 30 emit a collimated light beam 32 which includes at least one wavelength component Δλ, but may have a larger spectral width or different spectral profile. In the illustrated embodiment, the encoding takes place directly at the source through proper modulation thereof, but in a variant embodiment, a spatial modulator may be positioned downstream each source. Target, pre-modulated wavelength components from each source light beam 32 is selected through reflection by an appropriate dichroic mirror 37, or multi-wavelength partial reflector, placed at an angle (preferably 45 degrees) with respect to the light-guiding axis of the primary waveguide 44 along a common axis, thereby multiplexing the reflected wavelength components into the encoded light signal 42. This encoded light signal is then coupled into the core 46 of the primary optical fiber 44 through focusing by a lens 38 having a focal length and position appropriate to the numerical aperture and dimension of the fiber core 46.

Figures 6A, 6B:
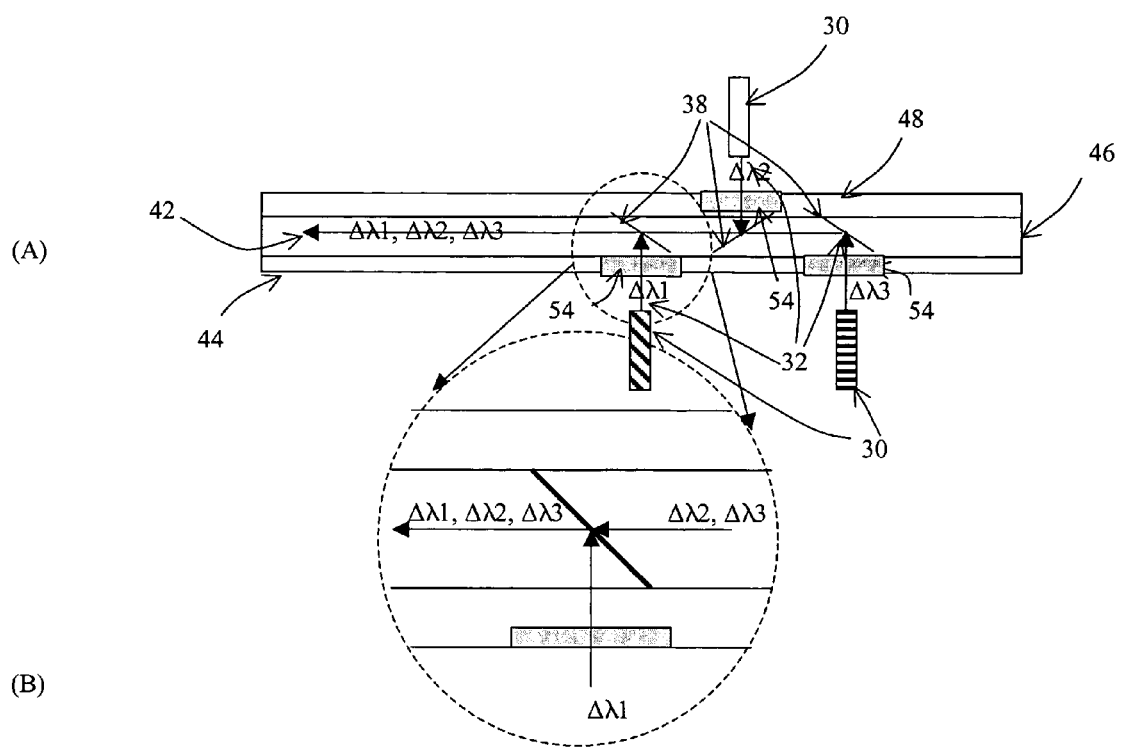
FIG. 6B is an enlargement of section A of FIG. 6.

Referring to FIGS. 6A and 6B, there is shown an alternative to the embodiment of FIG. 5 where the light sources 30 are positioned transversally to an input end of the primary optical fiber 44 at different positions along the length thereof, such that their modulated collimated light 32 is aligned with optically transparent windows 54 provided in the cladding 48 of the primary waveguide 44. Thus, the source lights 32 are directly transmitted through the optical windows 54 into the core 46 of the primary waveguide 44 where the appropriate wavelength components are selected and multiplexed by reflection using dichroic mirrors 38 provided directly in the core of the primary waveguide. To optimise coupling of the collimated sources 30, lenses (not shown) can be placed between the sources 30 and the optical windows 54. The focal length of the lenses should be appropriate to the numerical aperture and dimension of the fiber core 46

According to another preferred embodiment (not shown), modulated collimated light from light sources may be first individually coupled into small waveguides. These small waveguides may then be bundled and simultaneously coupled into a larger primary waveguide.

All of the embodiments described above provide different manners of sending an encoded multiplexed light signal into the input end primary waveguide. It is of course understood that other assemblies achieving the same result would also be considered within the scope of the present invention.

Figure 7:
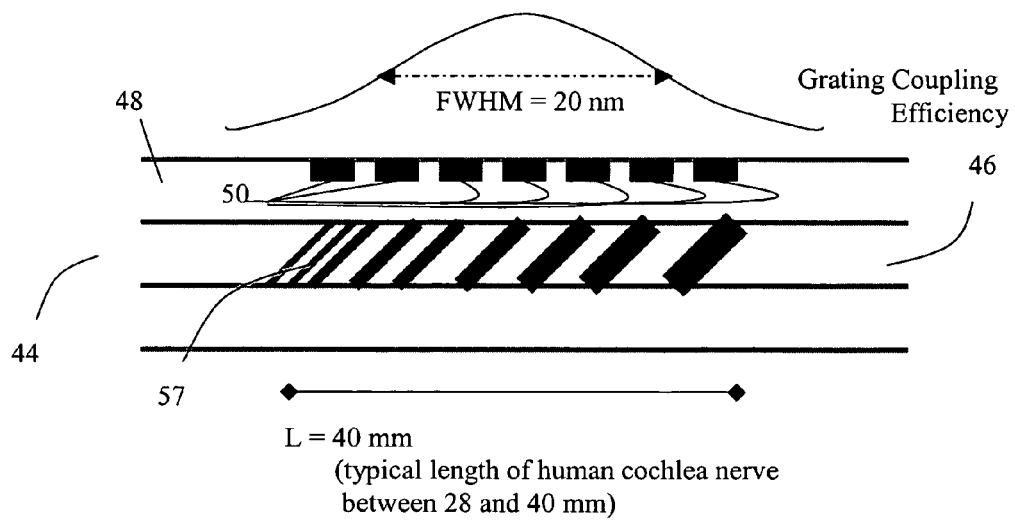
FIG. 7 is a cross-sectional side view of the output end of a device according to a preferred embodiment of the invention, showing a blazed optical grating comprising a number of uniform Bragg gratings positioned at output positions along the light guiding axis.
Figure 13:
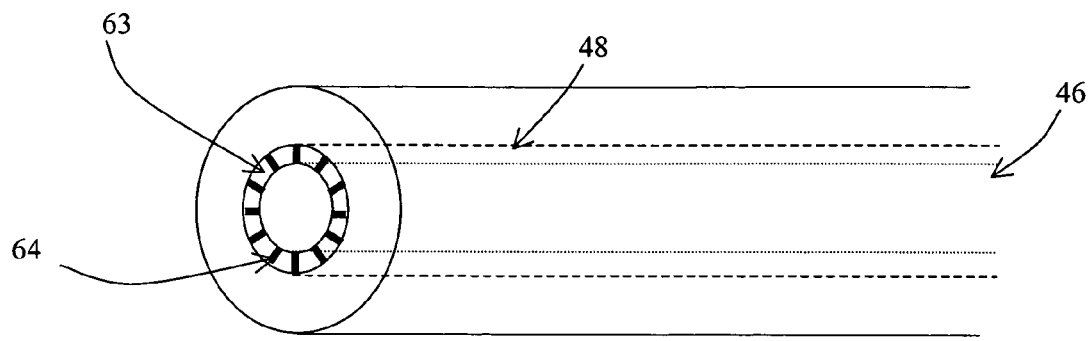
FIG. 13 is a partially transparent perspective side view of a micro-structured optical fiber having an air cladding composed of a number of air gaps and fused silica bridges, according to a preferred embodiment of the invention.

In one preferred embodiment, for example shown in FIG. 7, the optical waveguide 44 is a conventional fiber having a cladding 48 and a core 46. In another embodiment, illustrated in FIG. 13, the optical fiber 44 is a micro-structured fiber having an air cladding 48 composed of air gaps 63 and fused silica bridges 64. Such an optical fiber allows a greater numerical aperture and thus higher modes of electromagnetic radiation (i.e., light) and greater light coupling capabilities. In both case, the core 46 of the fiber 44 defines its light-guiding axis. Coupling of the encoded light signal at the input end of the primary waveguide may be accomplished in any appropriate manner, as will be readily understood by one skilled in the art. The length of the primary waveguide is preferably selected as a function of the required distance to the target stimulation sites for a given application of the invention.

The outcoupling of the encoded light signal at the output end of the primary waveguide will now be described according to several preferred embodiments of the invention.

Referring to FIG. 7, the output end of the primary waveguide of a device according to a preferred embodiment of the invention is shown. Outcoupling means for transversally coupling each wavelength component of the encoded light signal out of the primary waveguide 44 at a different output position 50 along the light-guiding axis are provided. In the embodiment of FIG. 7, the outcoupling means include at least one reflecting element, preferably an optical grating 57. The optical grating may be a Bragg grating which is chirped so that different wavelengths are deviated, or reflected, at different positions along the fiber 44, and blazed (the fringes are at an angle with respect to the propagation axis) so that the deviated wavelengths are coupled out of the fiber 44 through its cladding 48. Standard, non-chirped, blazed Bragg gratings at different wavelengths may also be used if they are placed at different positions along the fiber. Long-period gratings may also be a preferred embodiment if the density of output positions 50 is not important and if the spectral linewidth of the outcoupled light can be wider.

Figure 8:
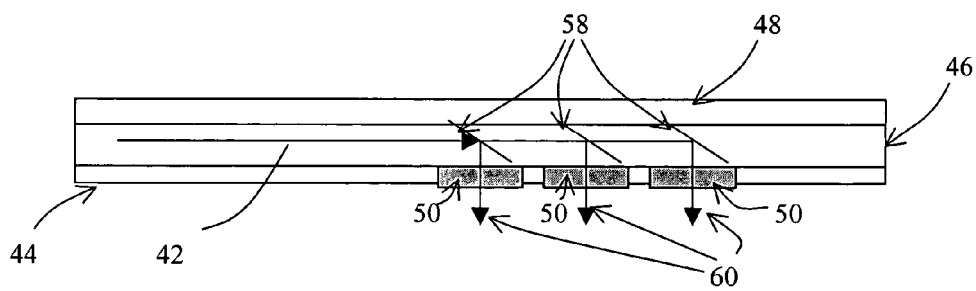
FIG. 8 is a cross-sectional side view of the output end of a device according to another preferred embodiment of the invention, showing a number of dielectric reflectors positioned at output positions along the light guiding axis.
Figures 9A, 9B:
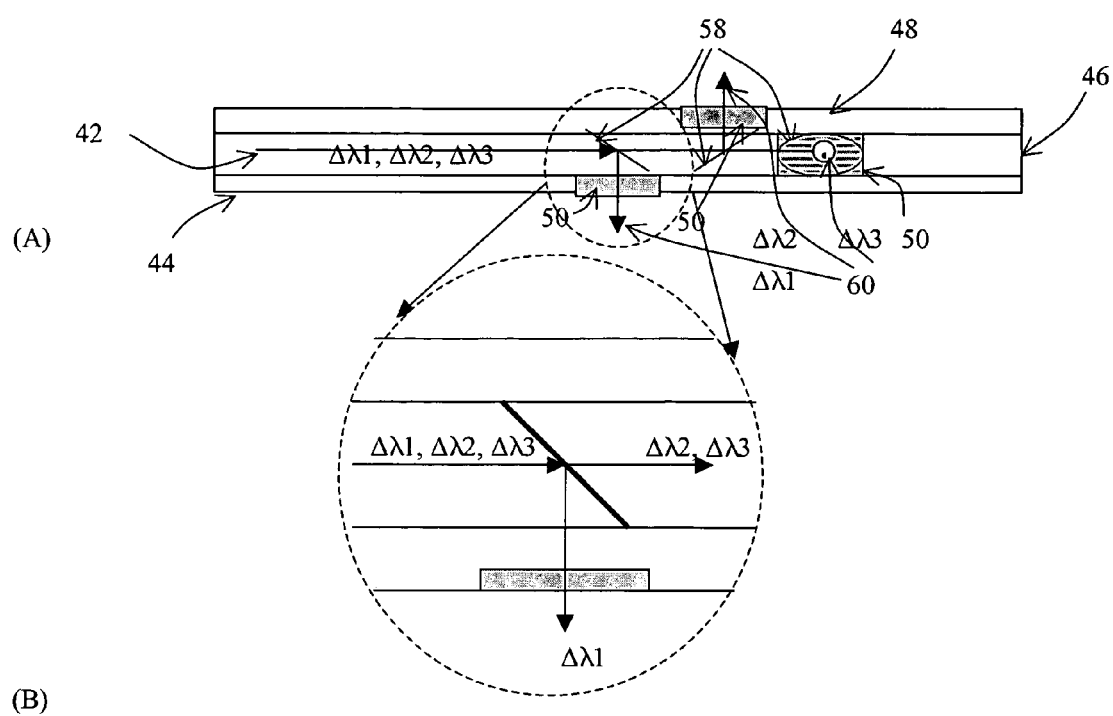
FIG. 9B is an enlargement of portion A of FIG. 9.

In other preferred embodiments shown in FIGS. 8 and 9, the output coupling means include dielectric reflectors 58 placed at an angle inside the fiber core 46. Each dielectric reflector 58 reflects a specific wavelength with a specific linewidth so that only part of the spectrum is coupled out of the fiber 44 through its cladding 48. A thorough description of the method and means used to introduce reflective and/or refractive components in an optical fiber is given in assignee's U.S. patent application filed on the 21 of Oct. 2005, entitled "Optical Fiber Devices Using Component Insertion" by inventors René Beaulieu, Daniel Cantin, and Marc Levesque, which is incorporated herein by reference.

Figure 10A:
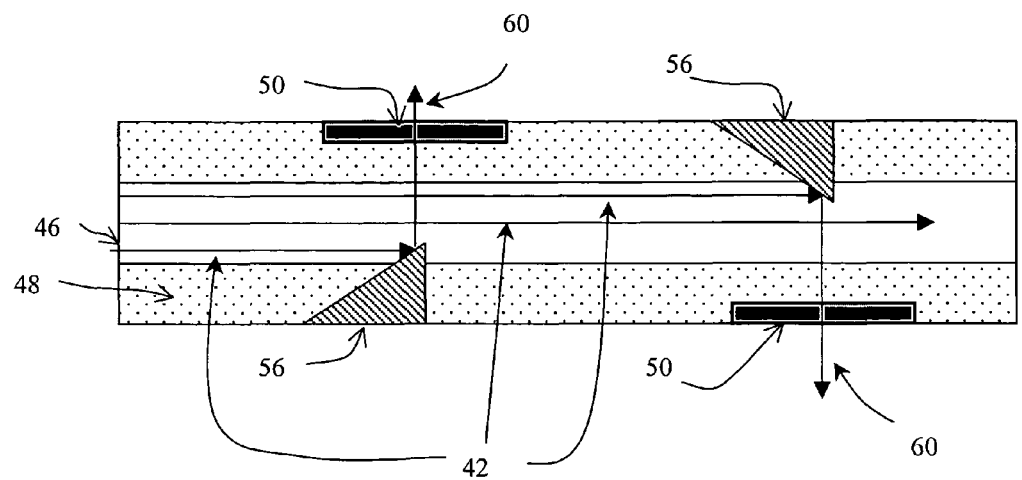
FIG. 10A is a cross-sectional side view of the output end of a device according to yet another preferred embodiment of the invention, showing outcoupling means which use shaping in the device core to reflect part of the encoded light signal out of the waveguide core.

In yet another preferred embodiment illustrated in FIG. 10A, shaping of the waveguide core 46 and cladding 48 is used to provide reflecting elements 56. These reflecting elements 56 reflect specific wavelength components of the encoded light signal 42 towards output positions 50 and out of the fiber core 46. Alternatively, according to the embodiment of FIG. 10B, shaping in the waveguide core 46 provides refracting elements 59 to refract specific wavelength components of the encoded light 42 through output positions and out of the fiber core 46.

Figure 11:
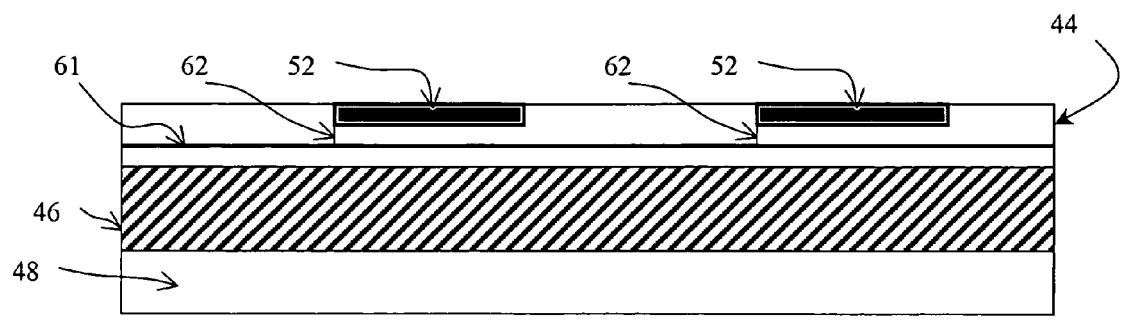
FIG. 11 is a cross-sectional side view, according to a preferred embodiment of the invention, of an electrical wire extending along the primary waveguide and used to apply a polarization voltage to the photoelectric material of the electrodes.

For a number of applications, it is desirable to transform the optical stimulation information in each wavelength component into an electrical stimulation signal, Referring to FIG. 11, localized electrodes 52 may be provided on the outer surface of the primary waveguide for this purpose. The electrodes are preferably composed of layers of photoelectric material deposited at the output positions 50 where light is coupled out of the fiber 44. The expression "photoelectric material" generally refers to a material whose electric properties are affected by exposure to light and includes photovoltaic and photoconductive material. Photovoltaic materials are capable of producing a voltage when exposed to electromagnetic radiation. Electrical conductivity of photoconductive material is affected by exposure to electromagnetic radiation. Preferably, this photoelectric material is biocompatible with the cells of the tissue to be stimulated.

Figure 12:
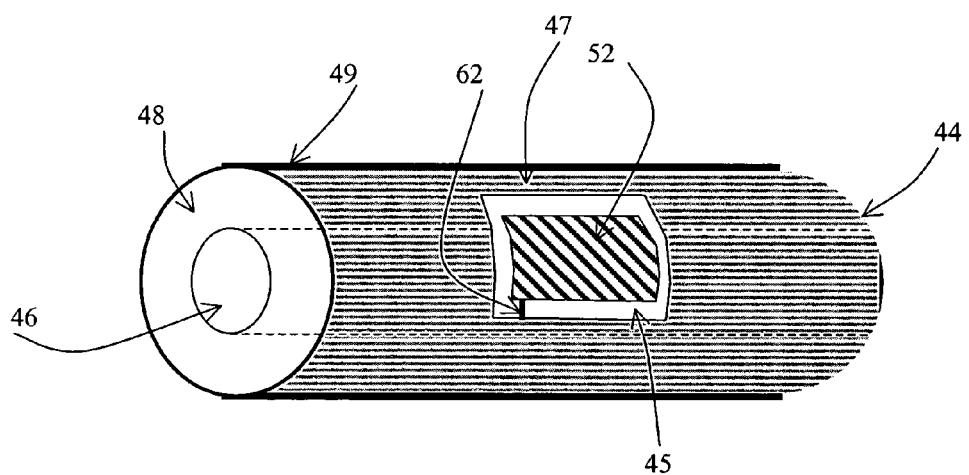
FIG. 12 is a partially transparent perspective side view of the output end of a device according to yet another embodiment of the invention, showing a metallic cladding of the primary waveguide in electrical contact with the photoelectric material of the electrodes.

In the particular case of photoconductive material, means to apply a polarization voltage to the fiber 44 are also provided. One of these means, shown in FIG. 11, could be the use of a small electrical wire 61 running along the fiber cladding 48 and making electrical contact 62 with the photoconductive material. Laser micro-machining could be used to produce a groove along the fiber 44 in order to insert the small electrical wire 61. Another means would be to micro-machine, preferably with a laser, a slot along the fiber-preform cladding 48 that would produce a groove for the electrical wire 61 once the preform is pulled into an optical fiber 44. Finally, in another preferred embodiment shown in FIG. 12, the glass cladding 48 of the optical fiber 44 can be covered with a metallic cladding 47 that can be laser-machined to create an electrical contact 62 with the photoconductive material 52. In this case, the metallic cladding 47 would be covered, or coated, with a non-conductive material 49 to ensure its electrical insulation outside of the electrode regions. In the preferred embodiment of FIG. 12, laser micro-machining techniques are used to provide grooves 45 in the metallic cladding 47 of the fiber 44 which receive the electrodes 52. In another preferred embodiment, grooves with a small length extent are made in the preform to be pulled into an optical fiber and when the pulling of the fiber is performed these grooves extend to fit the length of the electrodes to be put on the fiber. If a photovoltaic material is used for the electrodes, it preferably includes GaAs crystal, which is preferred over silicon crystal owing to the smaller thickness required to achieve the same efficiency. Silicon crystal usually requires a thickness of several hundreds of microns to obtain energy conversion efficiencies of over 10% while only a few microns are sufficient in the case of GaAs. However, thin film materials produced through deposition processes are preferable over crystalline material since the required thickness can be one micron or less owing to its higher absorptivity. Furthermore, the bonding of the electrode material to the fiber is also much easier in the case of thin film materials since they can be directly sprayed into the laser micro-machined grooves of the optical fiber. The energy conversion efficiency of the material in thin film form is however less than that in crystalline form. New materials such as photoconductive and photovoltaic polymers [for example, poly(p-phenylenevinylene (PPV)] and dye-integrated titanium dioxide ($TiO_2$) could shortly become preferred materials given their ease of integration into the optical fiber grooves. Many polymers could be integrated through wet coating processes while $TiO_2$ could be integrated with standard vacuum deposition processes. If signal response times of over a few milliseconds are required, a pyroelectric material, such as polyvinylidene fluoride (PVDF), may be preferable since it may be deposited easily using wet coating techniques and requires a thickness of a few tens of micrometers. Biocompatibility issues regarding the photovoltaic and photoconductive material of electrodes can be addressed by coating the photovoltaic and photoconductive material with biocompatible materials such as polyimide.

Each deposition area therefore defines an "electrode". The density of the electrodes provided on a given device depends on the selected manufacturing techniques. Depending on the application, with a typical 125 μm-diameter optical fiber, it is possible to achieve an array of electrodes, each measuring 200 μm long by 50 μm to 90 μm wide, and spaced by 50 μm, leading to a density of 40 electrodes/cm. Up to 160 electrodes can be arranged on a 40 mm length, allowing very high resolution with a very small diameter. Evidently, if the charge density needs to be below a given value, the electrode size can be adjusted accordingly.

In some cases, for example where the density of axonic terminals of nerve cells are clustered into ganglia, the use of electrical stimulation may be complicated by the simultaneous creation of extraneous stimuli. Although an aim of multi-electrode implants is improvement in the specificity of the stimulation, the real advantages to using multi-electrodes are limited by the current required to attain the threshold of perception. The current required is often greater in the case of closely spaced multi-electrodes than for farther spaced single electrodes. This leads not only to increased extraneous stimuli, thus defeating the purpose, but to increased risk of injury to the patient.

Figure 10B:
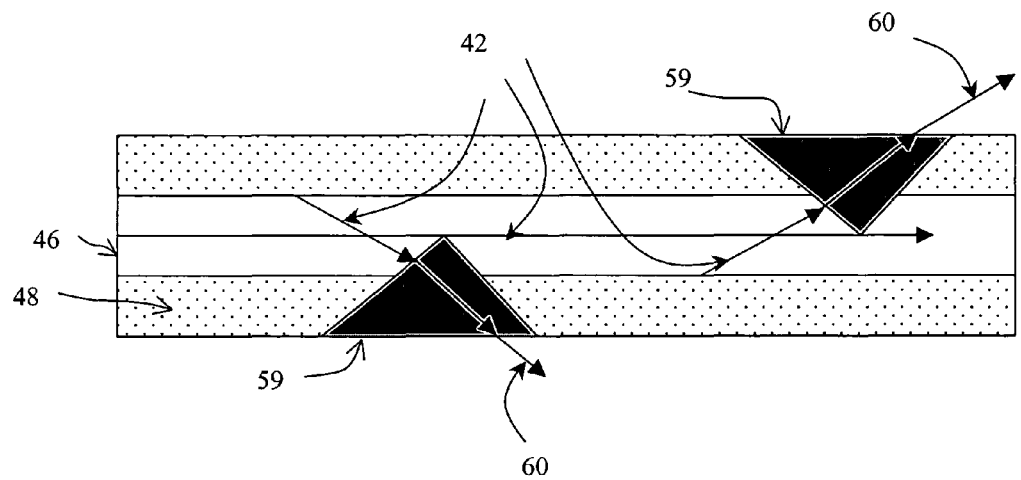
FIG. 10B is a cross-sectional side view of a refractive variant to the embodiment of FIG. 10A.
Figure 14A:
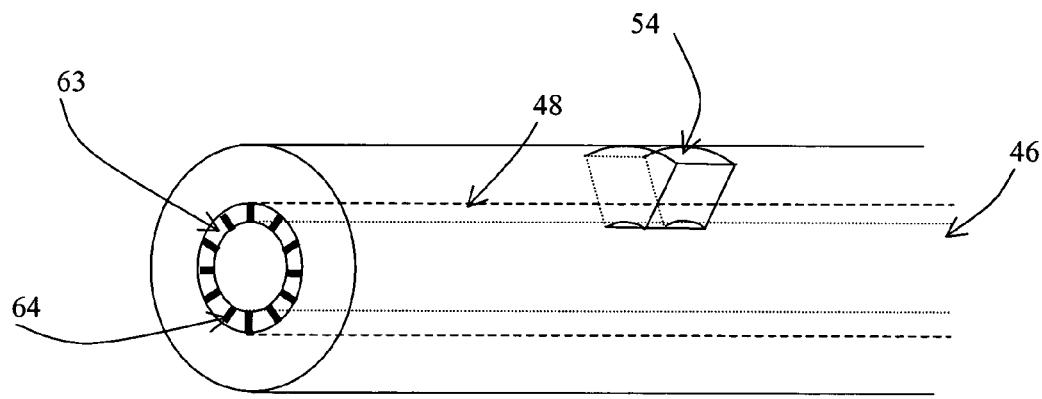
FIG. 14A is a partially transparent perspective side view of a micro-structured optical fiber having an air cladding composed of a number of air gaps and fused silica bridges with part of the cladding drilled and filed with an optically transparent material, according to a preferred embodiment of the invention.
Figure 14B:
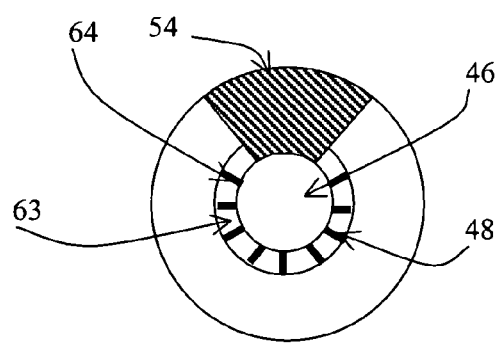
FIG. 14B is cross-sectional view of the micro-structured optical fiber of FIG. 14A.

One alternative to the problems of specificity and injury inherent with electrical stimulation is photo-stimulation. As suggested by an embodiment of the invention illustrated in FIGS. 14A and 14B, the electrodes 52 used in transmitting stimulation information signals to the stimulation sites may be replaced by optical windows 54 provided in the primary waveguide 44 at the output positions 50 of the wavelength components of the encoded light signal 42. These optical windows 54 allow the light stimulation signal to be transversally coupled out of the optical fiber 44 by refraction as illustrated in FIGS. 10B, 14A and 14B or by reflection as illustrated in FIGS. 7 to 10A. According to the embodiment of FIG. 14, an optical window 54 may be produced in the side of a primary waveguide 44 by laser micromachining through the cladding 48 of the waveguide 44 and filling an air gap 63 with appropriate optically transparent material, such as silica glass. According to another preferred embodiment, the optically transparent material defining the optical window 54 may simply be the optically transparent material of the optical waveguide 44 or fiber cladding 48 itself, providing it is made of a transparent material. In another preferred embodiment, the optical window is made of a material having a refractive index higher than the refractive index of the fiber core so as to increase the output coupling efficiency through the optical window. In yet another embodiment, the optical window is made of material, which may include a dielectric coating that transmits specific wavelengths of light, for example those corresponding to specific photoactivated molecules, while reflecting others. Finally, these preferred embodiments of an optical window may be combined in such a way as to optimize the desired results with respect to the requirements of the application.

Figure 15A:
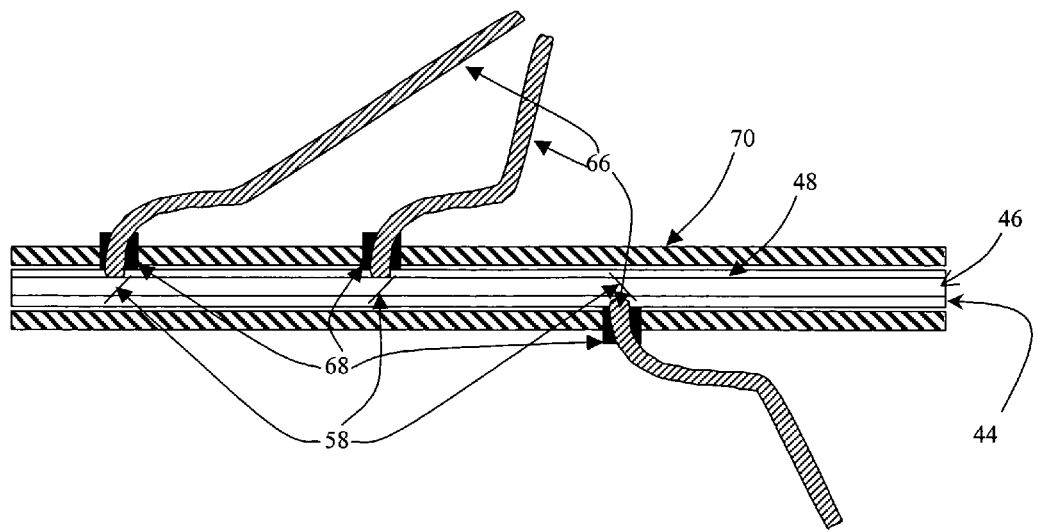
FIG. 15A is a cross-sectional side view of the output end of a device according to an embodiment of the invention, showing the use of secondary fibers coupled to output positions along the primary optical fiber and outcoupling light to stimulation sites located away from the primary optical fiber.
Figure 15B:
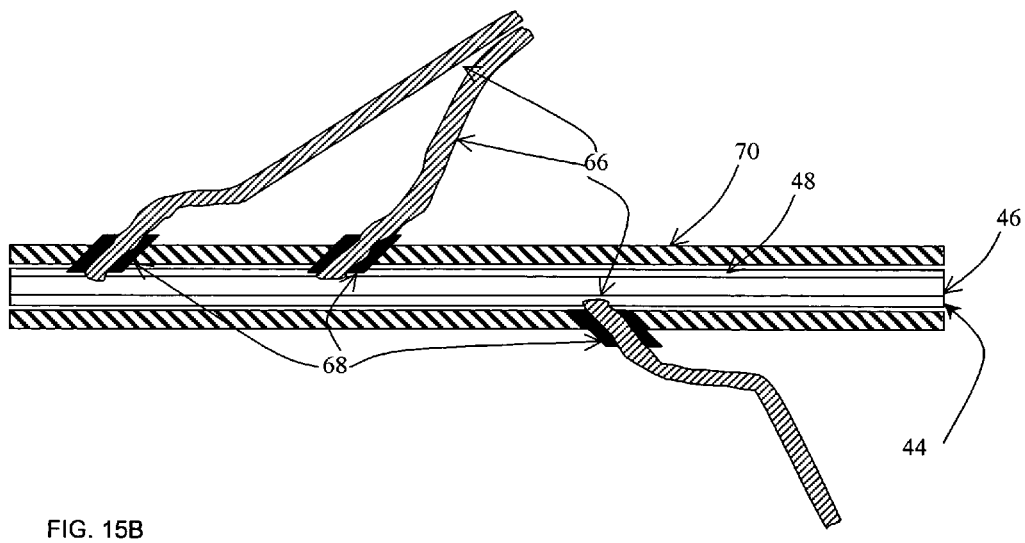
FIG. 15B is a cross-sectional side view showing the use of secondary fibers according to a different embodiment of the stimulation device.

One other option, illustrated in FIGS. 15A and 15B, is to use secondary waveguides 66 attached to the core 46 of the primary waveguide 44 at output positions 50. The optical windows on the primary optical fiber may be used as the entry windows to the secondary optical fibers. The secondary waveguides may be fused 68, preferably using silica powder as fusing agent, to the secondary waveguides 66 at the output positions 50. In FIG. 15A, dielectric reflectors 58 ensure the coupling of light out of the primary fiber 44 and into the secondary fibers 66. The coupling of light into the secondary fiber 66 can be done through refraction means, by attaching the secondary fibers 66 to the primary waveguide core 46 at an angle, as shown in FIG. 15B, and matching the numerical apertures to the primary fiber 44. The use of secondary fibers is particularly advantageous in cases where more specific or accurate positioning of the outcoupled light and/or access to more distant sites is necessary. The secondary fibers are ideally smaller than the primary fiber so that the distal part of the device remains compact allowing precise positioning without damaging the environment at sites of interest during the implantation surgery. Such damage can render the device completely inoperative. In general, the connection between the primary fiber and the secondary fibers may be done through laser micro-machining, including ablation and fusion processes. The use of laser micro-ablated "V" grooved substrates that help to manipulate and align the fibers with respect to one another is preferred. Once the alignment is properly done, the fibers can be attached to the primary fiber and/or the substrate, preferably by laser fusion. In the preferred embodiment illustrated in FIGS. 15A and 15B, a capillary 70 is placed around the primary fiber 44 to allow the attachment of a secondary fiber using laser fusion 68. Holes are drilled into the sides of the capillary 70 up to the core 46 of the primary fiber 44 to allow the passing through of the secondary fibers 66 prior their fusion. The assembled fibers can then be packaged into a single device that can be implanted in a patient. This type of packaging provides added robustness to the device, since the primary fiber may be weakened following the laser ablation and/or fusion processes used to attach the secondary fibers thereon. The secondary fibers which are kept intact are less susceptible to breakage, more flexible, and can be coated with a material that enhances their robustness, such as polyimide which is also biocompatible. In the previous embodiments, the secondary fibers, preferably their distal ends, may be equipped with electrodes composed of photoconductive or photovoltaic materials for electrical stimulation.

In the following description the term "photoactivated molecules" refers to both caged molecules that become uncaged (or released) or are made chemically or biochemically active when illuminated by light at specific wavelengths, and molecules that reflect, absorb, or reemit characteristic luminescent light when illuminated with light of specific wavelength. These photoactivated molecules may be biochemical compounds, such as hormones, enzymes, neurotransmitters, etc, or molecules caged in quantum dots, micro-spheres, nanoshells, micelles or combinations of these.

Figures 16A, 16B:
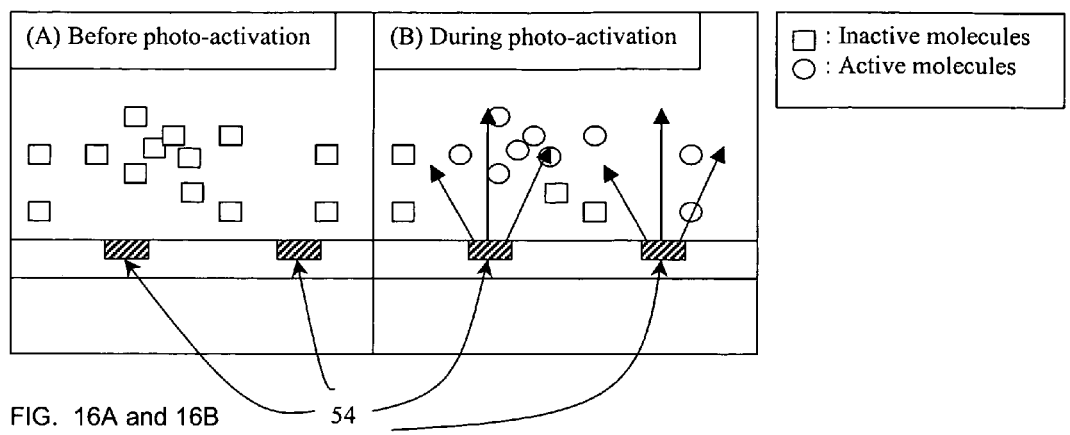
FIG. 16A is a schematic illustration of a situation before induction of the photoactivation process of molecules.
FIG. 16B is a schematic illustration of the situation during induction of the photoactivation process.
Figures 17A, 17B:
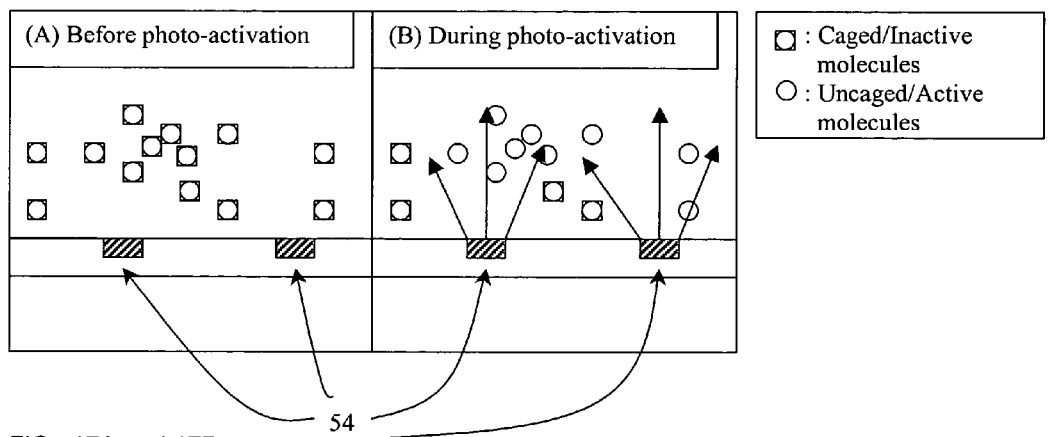
FIG. 17A is a schematic illustration of a situation before induction of the photoactivation process of caged molecules.
FIG. 17B is a schematic illustration of the situation during induction of the photoactivation process.
Figures 18A, 18B:
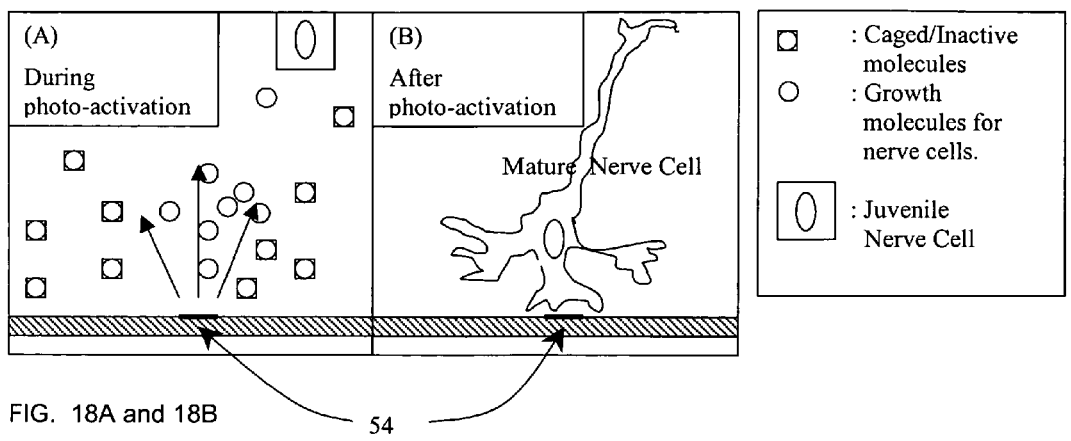
FIG. 18A is a schematic illustration of a situation during induction, by a preferred embodiment of the invention, of the photoactivation process of caged molecules which act as a growth and/or migration factor for neurons (J. Q. Zheng, Nature, vol. 403 (2000) p. 89; US Patent Publication No. 2005/0203601; US Patent Publication No. 2002/0051806).
FIG. 18B is a schematic illustration of the situation after induction of the photoactivation process.
Figures 19A, 19B:
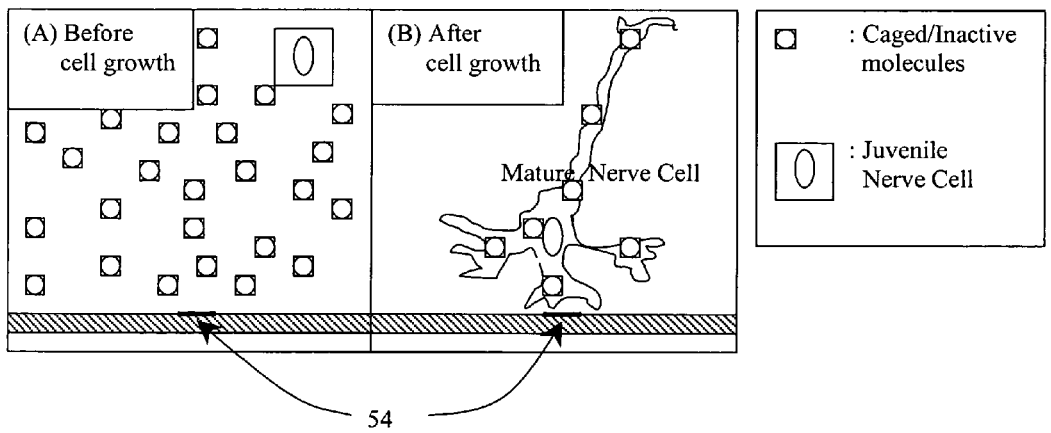
FIG. 19A is a schematic illustration of a situation where molecules capable of being photoactivated (or nanoshells, micelles, quantum dots) are present in the immediate environment of a juvenile nerve cell.
FIG. 19B is a schematic illustration of a situation where these molecules have been taken up by the mature nerve cell during the growth phase and may now be photoactivated by a preferred embodiment of the stimulation device placed near the nerve cell.
Figures 21A, 21B:
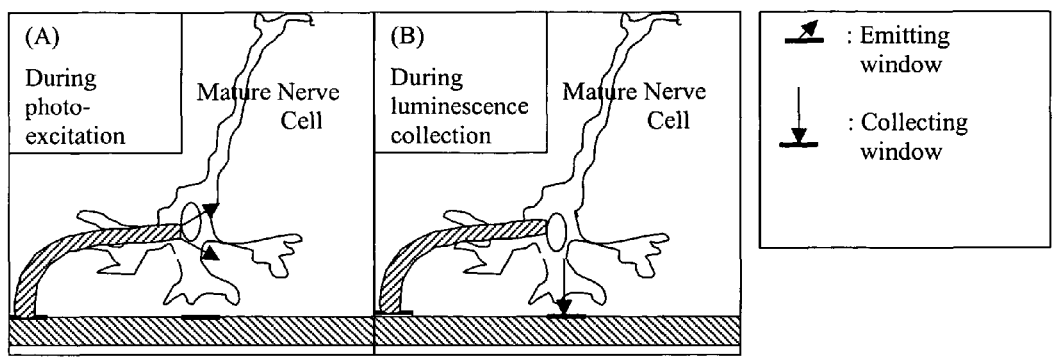
FIG. 21A is a schematic illustration of a photo-excitation process of molecules taken in by a mature nerve cell induced by another preferred embodiment of the stimulation device.
FIG. 21B is a schematic illustration of the monitoring of the luminescence response of the photo-excitation process using this preferred embodiment of the stimulation device.
Figure 22:
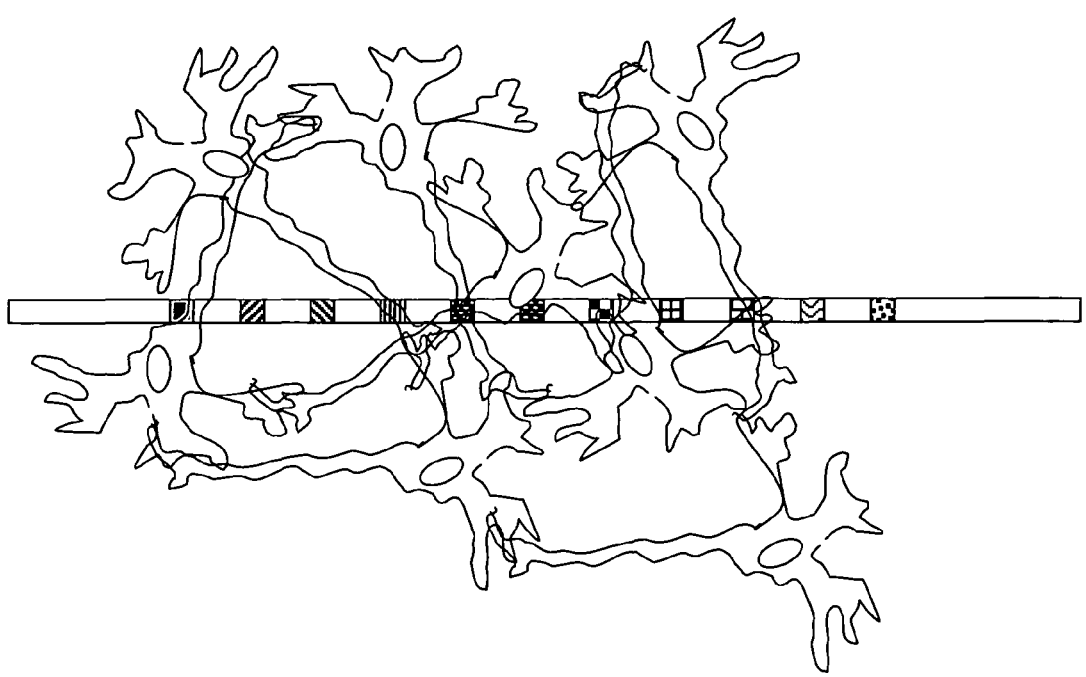
FIG. 22 is a schematic illustration of a preferred embodiment of the stimulation device showing its use as a means to study living nerve tissue.

Light coupled out of the waveguide can be used to photoactivate specific molecules which then directly or indirectly stimulate or inhibit specific cell, tissue, or system functions. The wavelength of the light is chosen to match the photoactivation wavelength of the photoactivated molecules. In this case, modulation of the intensity of the light source will allow the modulation of the stimulation or inhibition of the function to be controlled. FIGS. 16-18 depict the photoactivation of caged molecules, such as those used in the regulation of cell growth and migration, placed in the vicinity of the cells to be stimulated or inhibited to maximise the coupling between the fiber and the cells and increase its stimulation efficiency. FIGS. 19A and 19B depict the uptake of originally inactive but photoactivatable molecules by a nerve cell during growth. Cell processes in the nerve cell may be studied through either monitoring of luminescent molecules which are uncaged by certain nerve cell functions (such as nerve impulse) and thus act like markers or measurement of changes in physical and chemical properties (such as electrical activity) of the nerve cell resulting from the photoactivation of specific molecules. FIG. 21 shows the use of a secondary fiber to more specifically photoactivate molecules (or excite luminescence) in a certain region of the nerve cell. FIG. 22 is a schematic illustration of a preferred embodiment of the stimulation device showing its use as a means to study living nerve tissue grown in culture.

Figures 23A, 23B:
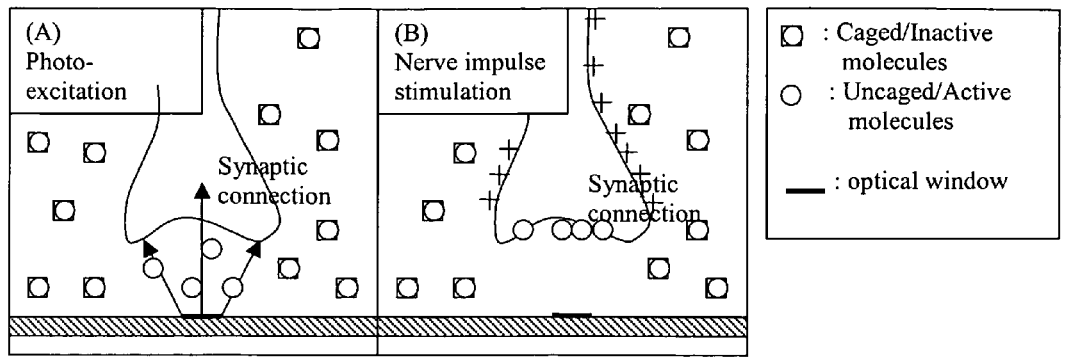
FIG. 23A is a schematic illustration of a situation where specific molecules in the vicinity of the nerve synapse are photoactivated by a preferred embodiment of the stimulation device.
FIG. 23B is a schematic illustration of the photoactivated molecules which transmit a nerve impulse by migrating to the nerve synapse and stimulating an action potential.

The case of neurostimulation, stimulation or inhibition that may be produced via photoactivation of molecules corresponding to neurotransmitters specific to the ganglion cells (or neuron types) to be stimulated, is shown in FIG. 23. These molecules are biochemically inactive (or caged) prior to being illuminated. Under specific wavelength illumination, the caged molecules undergo either a structural or chemical change that makes them chemically active in the environment of the cells to be stimulated or inhibited. In another preferred embodiment, the active molecules are placed inside microspheres, quantum dots, micelles, or nanoshells made of bio-resistant and bio-inert materials that change properties upon illumination. Under illumination at specific wavelengths the bio-resistance of the micro-spheres decreases and the caged molecules are released and become active.

These caged and photoactive molecules need to be placed in the vicinity of the cells to be stimulated or inhibited so that they may perform their expected functions properly. This may be accomplished by fabricating a channel in the primary waveguide along its length. The molecules would then be injected in solution form into the channel, exit the channel through a small opening in the optical fiber at the output position and thus be placed in the vicinity of the stimulation site. If micro-structured fibers are used (see FIGS. 13 and 14), one or more of the air gaps in the fiber can be used as injection channels much in the same manner. Another means of introducing the molecules is through conventional injection into the blood stream of a solution containing the molecules, providing that the molecules can reach the specific stimulation area through this scheme. Otherwise, the molecules may be injected directly into the specific area to be stimulated using a syringe.

Figures 24A, 24B:
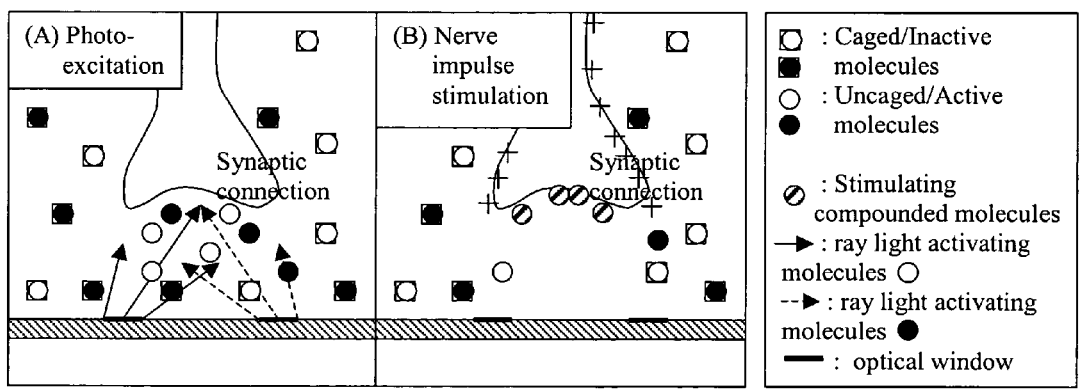
FIG. 24A is a schematic illustration of a situation where different specific molecules in the vicinity of the nerve synapse are photoactivated by the different wavelengths of light coupled out of the primary waveguide of a preferred embodiment of the stimulation device.
FIG. 24B is a schematic illustration of new molecules, created from the reaction of the photoactivated molecules, which have migrated to the nerve synapse thereby stimulating a nerve impulse.
Figures 25A, 25B:
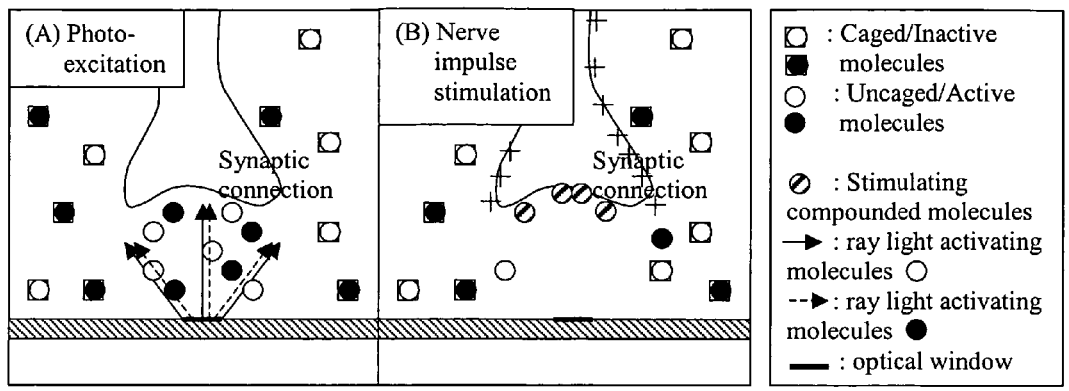
FIG. 25A is a schematic illustration of a situation where different specific molecules in the vicinity of the nerve synapse are photoactivated by the different wavelengths of light coupled out of the same optical window of the primary waveguide of a preferred embodiment of the stimulation device.
FIG. 25B is a schematic illustration of new molecules, created from the reaction of the photoactivated molecules, which have migrated to the nerve synapse thereby stimulating a nerve impulse.

In one preferred embodiment, illumination of different molecules at different wavelengths may preferably be performed simultaneously. Consider, for example, the case where two neurons are located in proximity to one another and the stimulation process of a particular neuron is independent of the stimulation process of another neuron. It is possible to photoactivate this particular neuron by using light of a given wavelength to photoactivate specific molecules in the vicinity involved in its stimulation and to photoactivate the other neuron by using light of a different given wavelength to photoactivate different specific molecules also in the same vicinity but which are involved in the stimulation of this other neuron. In this way, the stimulation of both neurons may occur simultaneously but yet independently—there is no need to carry out the photoactivation at different times in order to limit crosstalk-like behaviour. In another preferred embodiment, the illumination at different wavelengths is performed sequentially. For example, if one photoactivated molecule needs to be put in the presence of another photoactivated molecule to become effective, the illumination at the photoactivation wavelength of the first molecule will have to be performed prior to, or simultaneously with, the illumination of the second photoactivated molecule at the second wavelength. This is illustrated in FIGS. 24 and 25.

In some cases, it is known that light can stimulate the process of cellular growth (J. Q. Zheng, "Turning of nerve growth cones induced by localized increases in intracellular calcium ions", Nature, vol. 403 (2002) p. 89). This may be done by using specific photoactivated growth factors (e.g. molecules, proteins or hormones) to stimulate the growth of a specific type of cell placed in the immediate vicinity of the outcoupled light of the present device. For best results, stem cells may be added to the site at the time of surgical implantation of the device. This would be especially beneficial especially for cells that do not naturally grow or divide in adult patients, for example neurons. This is illustrated in FIGS. 18 and 19. Using this process, the coupling efficiency of the implanted device with the natural neuronal network may be increased by making specific neurons grow toward the light outputs of the device.

Figures 20A, 20B:
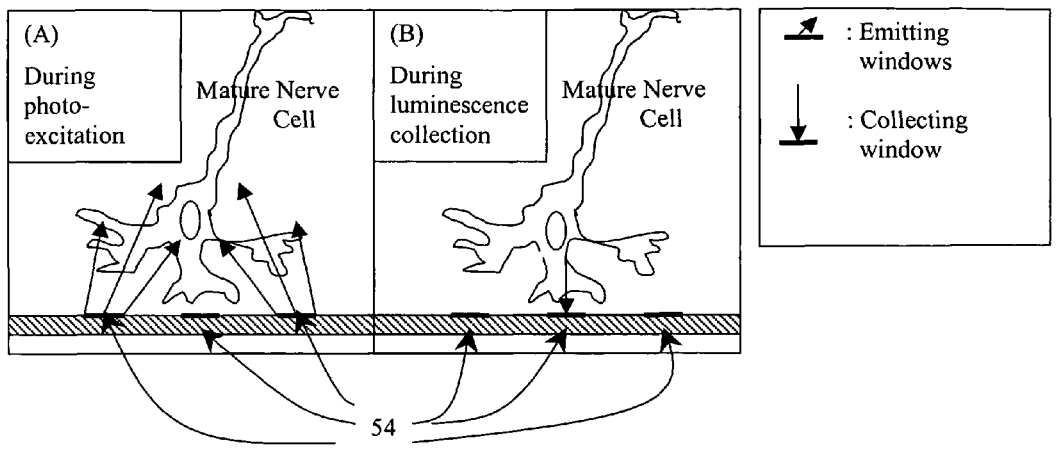
FIG. 20A is a schematic illustration of a photo-excitation process of molecules taken in by a mature nerve cell induced by a preferred embodiment of the stimulation device.
FIG. 20B is a schematic illustration of the monitoring of the luminescence response of the photo-excitation process using this preferred embodiment of the stimulation device.

Cells that contain photo-luminescent molecules, either naturally or by induced uptake (see FIGS. 18 and 19) can be used to monitor cellular activities. These molecules may be strategically chosen to control some of the cellular functions through direct or indirect detection of their presence, for example detection through luminescence. Accordingly, this process could be used to monitor the nerve impulse in neurons through polarisation of calcium, potassium or other ions or through the presence of neurotransmitters at synaptic connections indicating neuronal activities of specific neuron cells. This method may be used to replace in lieu of electrical stimulation of neurons using implanted electrodes to detect nerve impulse. In this case, the proposed invention is used to provide illumination at the excitation wavelength from the proximal end to the photo-luminescent molecules at the distal end and the luminescence signal emitted by the molecules is collected by the same device (see FIGS. 20 and 21) working with light traveling in the opposite direction e.g. to the proximal end. The luminescent light can then be detected and analysed to measure the nerve impulse. To obtain the best results, the preferred embodiment uses, at the distal end of the device, output and input coupling techniques that are not dependent on the wavelength or dichroic components that can handle both the excitation and luminescence wavelengths. The same techniques described in preferred embodiments used to couple out the light at the distal end can be used to couple the luminescent light into the fiber up to the proximal end. Another preferred approach, illustrated in FIG. 20, is to use two optical windows to provide illumination at the excitation wavelength and to collect the luminescence by a third window placed between them. The excitation illumination can be performed with dielectric mirrors having high reflectivity at the excitation wavelength while the collection of the illuminescent light via the collecting window can be performed using a dielectric mirror having a high reflectivity at the luminescence wavelengths. Another approach illustrated, in FIG. 21, is to use a secondary fiber to provide the excitation wavelength and a window in the primary fiber to collect the luminescent light. Yet another preferred approach is to use one secondary fiber to provide the excitation wavelength and another one to collect the luminescence. In this case, the two secondary fibers are placed in close vicinity to each other to ensure sufficient luminescent signal collection (see FIG. 15). This monitoring technique of luminescent signal related to specific biochemical concentration in the body can allow to diagnose pathologies, control concentration levels or presence of some compounds (glucose, iodine, . . . ), or type of cells (cancerous cells, stem cells, . . . ), or to stimulate their growth in a specific type of tissue while combined with photoactivated growth factors.

Photoactivated molecules can be used either directly or indirectly. Direct use of photoactivated molecules implies that once molecules are activated they will react chemically or biochemically with a cell to stimulate or inhibit one of its functions. Indirect use implies that once the molecules are activated they will react or combine with one or many other molecules to produce a chemical or biochemical compound that will react with the cell to stimulate or inhibit one of its functions. One preferred embodiment of direct use of photoactivated molecules is a photoactivated neurotransmitter that could be used to initiate the stimulation of a nerve impulse to neuron cells, as shown in FIG. 23. One preferred embodiment of indirect use of photoactivated molecules is a photoactivated molecule that will combine with another molecule that could be naturally present or injected in the body to form an antagonist of neurotransmitter that could be used to inhibit the stimulation of a nerve impulse to neuron cells. Another preferred embodiment of indirect use of photoactivated molecules is the use of two different photoactivated molecules that will be activated at different wavelengths and that combine together to form a molecule that stimulates or inhibits a cell function, as shown in FIGS. 24 and 25. Yet another preferred embodiment of indirect use of photoactivated molecules relates to a caged molecule that can be uncaged (or released) through photoactivation by one or more specific wavelength components, but that becomes biologically active only once it is photoactivated by one or more different wavelength components. Some examples of applications of photoactivated molecules include: control of insulin for diabetics (monitoring and photoactivation), control of the level of iodine compounds for hypo- and hyper-thyroidism (monitoring and photoactivation), photodynamic therapy (creation of compounds that can specifically link and kill cancerous cells through photoactivated molecules), and stimulation of the growth of a specific type of cell.

In another embodiment, light is used to provide heat at the distal end of the optical fiber. The heat can be directly provided to molecules or cells by using the scheme illustrated in FIG. 7, 8, or 9 to couple out light 60 at specific wavelengths that are absorbed by the molecules or cells. If the absorbed wavelengths are mainly converted into vibrational or rotational energy of the molecules rather than reemitted as photons at longer wavelengths, the absorbed light heats the molecules. This process is more likely to occur at wavelengths in the infrared portion of the electromagnetic spectrum. One other preferred embodiment for providing heat uses an indirect heating process through the heating of a material at the output position 50 placed on the cladding 48 of the fiber 44. The heated material can then be used to heat molecules or cells that are put into contact with it. The heating can be used to stimulate or inhibit specific cell functions in the vicinity of the fiber, activate specific molecules, or uncage caged molecules in micro-spheres, micelles, quantum dots or nanoshells that can be affected by heat. The use of other wavelengths that would not heat the fiber environment or the heating material placed on the fiber would allow to monitor results of the heating process or to identify the presence of molecules, cells, micro-spheres, micelles, quantum dots or nanoshells to be heated. This monitoring or identification process could be done from the analysis of collected light through the same point as the heating point on the fiber or through other adjacent points in ways similar to those illustrated in FIGS. 20 and 21.

It is also possible to use multiple points along the optical fiber where the light can be partly coupled out from the fiber to stimulate, or to monitor, similar or different cell functions. This way one optical fiber may have multiple devices connected to it that may be implanted at different places inside the body. The use of different wavelength bands for each device can allow to control independently the stimulation, or the monitoring, at each of the implanted positions inside the body.

Of course, numerous modifications or combinations of these preferred embodiments could be made to the device above without departing from the scope of the present invention.

Method and Applications

In accordance with one application of the present invention, an embodiment of the device described above may be used as a cochlear implant for transmitting auditory stimulation information to auditory neuron sites of the cochlea, in situ of a patient. Such a cochlear implant includes a light generating means for generating light having a number of wavelength components, an encoding means for separately encoding at least a portion of the auditory stimulation information into each of the wavelength components, and a multiplexing arrangement for multiplexing the wavelength components encoded by the encoding means into an encoded light signal. The cochlear implant further includes a primary waveguide having an input end operationally connected to the multiplexing arrangement for receiving the encoded light signal therefrom, a light-guiding axis for guiding the encoded light signal therealong and an output end adapted to be positioned proximate the auditory neuron sites of the cochlea. In addition to the above elements, the device also has outcoupling means provided at the output end of the primary waveguide. These outcoupling means transversally couple each of the wavelength components of the encoded light signal out of the primary waveguide at different output positions along the light-guiding axis, each of the output positions being coupled to one of the auditory neuron sites of the cochlea.

In one embodiment, the cochlear implant preferably includes a number of electrodes, each associated with one of the output positions, for transducing a corresponding wavelength component into an electrical stimulation signal. In another embodiment, the cochlear implant preferably includes an optical window in the primary waveguide at each of the output positions, in order to output an optical stimulation signal therefrom.

Figure 26:
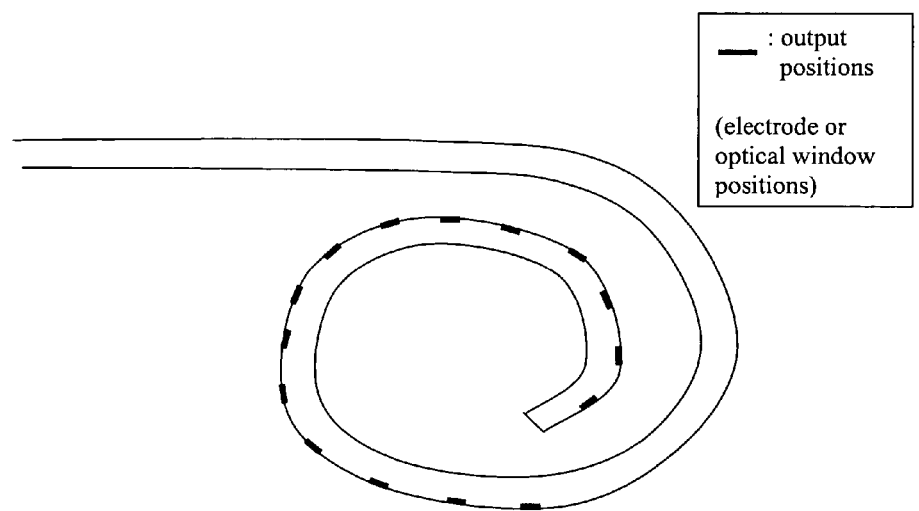
FIG. 26 is a schematic diagram of a preferred embodiment of the stimulation device of the invention illustrating the possibility of tailoring and fixing the shape of the optical fiber making it adaptable to cochlear implantation.

The present invention can provide great improvements to the technology of cochlear implants and address some of the drawbacks listed above. The greater number of electrodes afforded by the present invention helps to provide a greater resolution than most typical devices. Risk of injury to a patient's inner ear can also be reduced by using optical stimulation rather than electrical stimulation. Optical stimulation advantageously offers increased specificity through the use of optical fibers with diameters smaller than those achievable with traditional wires and safety given that optical fibers may be fabricated out of plastic or glass material, which is relatively inert. Optical fibers are also very flexible and are generally less subject to mechanical fatigue than metallic wire conductors. Furthermore, optical fibers can be overcoated with biocompatible materials minimising adverse reactions by host biological material and increasing the strength of the fibers while maintaining their compactness and flexibility. A preferred embodiment of the present invention as a cochlear implant is illustrated in FIG. 26. As shown, the flexibility of optical fibers allows to shape and adapt the implant to the particular structural anatomy of the patient. Such a shape could be made permanent by heating the fiber, preferably with a heat gun or a $CO_2$ laser, while it is rolled over a cylindrical or conical shape.

Cochlear implant knowledge and technology is continually changing and evolving. Research is underway to design implants that would help people with deafness due to surgical removal of their auditory nerves during tumor resection. These implants would stimulate the cochlear nucleus, the first stop after the auditory nerve in the auditory pathway to the brain. Some research is looking into implants that would stimulate the auditory nerve directly. The present invention would certainly be of benefit to such applications given the compactness of the device and the increased number of electrodes that may be implanted with a single device.

With reference to FIGS. 1, 7, and 8, the generation of an appropriate light signal in the particular application of a cochlear implant is illustrated. The multi-wavelength collimated light beam 32 coming out of a modulated light source 30 has its different wavelengths components ($\Delta\lambda 1, \Delta\lambda 2, \ldots, \Delta\lambda n$) spatially separated 36 by a dispersive element 34. The light coming out of the light source 32 is preferably collimated by standard collimation techniques adapted to the light source 30 used. The separated wavelengths components 36 are then redirected in a collimated beam 39 with the help of a cylindrical focusing element 38. The signal amplitude of each different wavelength ($\Delta\lambda 1, \Delta\lambda 2, \ldots, \Delta\lambda n$) is then individually controlled with a spatial light modulator (SLM) 40. The resulting collimated light beam with separated wavelengths having different signal amplitudes along its transverse direction is then multiplexed in a unique encoded light signal into the optical fiber 42 at the focal point 41 of another cylindrical focusing element 38. This control on the signal amplitude of each wavelength band ($\Delta\lambda 1, \Delta\lambda 2, \ldots, \Delta\lambda n$) allows to control the electrical signal level generated at each electrode 52 or to control the light signal level coupled out 60 at each location 50 along the optical fiber 44.

In a preferred embodiment, the light source 30 may include a light emitting diode (LED) having a spectral content extending from 15 to 40 nm or it may include a laser diode having similar extended spectral content. The light source 30 may be current modulated from a few hundred Hz up to 18 KHz to increase the stimulation response of the excited nerve cells and improve speech recognition of the implant patients. In one preferred embodiment, the dispersive element 34 is a blazed grating used in reflective mode. The separated wavelength components of the light source 30 are then collimated with the use of cylindrical focussing elements 38, preferably either a cylindrical mirror or lens 38. These cylindrical focusing elements 38 must be adapted to both the grating dispersion angle of the spectral content of the light source 30 and the dimension of the spatial light modulator 40. Different wavelength components 36 may then travel in parallel separated paths 39 and their signal intensity may be individually varied with the use of a linear spatial light modulator 40 composed preferably of a LCD linear array having refreshment rates from 120 to 400 Hz. The array will have a number of elements at least equal to the number of electrodes 52 (160 in the current example) on the optical fiber 44. Each element of the LCD array is used, for a specific wavelength, as a light attenuator in transmission mode that can be individually controlled. Another preferred spatial light modulator 40 is a linear array of micro-mirrors having dimensions in the range of 0.1-1 mm and capable of angle position changes in the range of 1 to 5 degrees. Each micro-mirror of this array will control the beam direction of a specific wavelength. A change in direction of the beam will modify the amount of light coupled into the optical fiber 44 at that specific wavelength and then to the corresponding specific electrode 52 on the optical fiber of FIGS. 7 and 8. Another cylindrical mirror or lens 38 is used to focus the collimated multi-wavelength encoded light signal 42 into the optical fiber 44 to form a multiplexed signal that will be demultiplexed by the blazed optical grating 57, or dielectric reflector 58, to provide the required signal to each output position 50.

The present invention is of course not limited to cochlear implants and may be applied to any number of electrical and optical stimulation technologies, old and new.

In accordance with another aspect of the present invention, there is generally provided a method for transmitting stimulation information to a plurality of stimulation sites. For example, these stimulation sites may be embodied by cerebral neuronal sites along a visual pathway—the stimulation information thereby stimulating a visual response, by muscle tissue sites whose contraction is to be stimulated or host tissue whose growth is to be stimulated. The use of biochemical compounds adapted for photoactivation by the wavelength components at these stimulation sites is also contemplated. These and more examples will be described in more detail further below.

The method generally includes the following steps of:

a. generating light having a plurality of wavelength components.

This may be accomplished by activating a plurality of light sources, each generating one of the wavelength components, or activating a light source generating a multi-wavelength light signal which includes these wavelength components.

b. separately encoding at least a portion of the stimulation information into each of the wavelength components.

If the wavelength components are generated by separate sources, this may for example be accomplished by directly modulating the amplitude of each generated wavelength component at the source. This modulation control may be timed so that the wavelength components are encoded simulatenously or sequentially.

If the wavelength components are generated as a multi-wavelength light signal, a step of separating said multi-wavelength light signal into said wavelength components may be performed between steps (a) and (b), so that the amplitude of each wavelength component may then be modulated separately.

c. multiplexing the wavelength components encoded by the encoding means into an encoded light signal.

This for example accomplished by placing a focussing element in the path of the wavelength components, or by any other appropriate technique known in the art.

d. guiding the encoded light signal along a light-guiding axis of a primary waveguide.

As mentioned above the primary waveguide is preferably an optical fiber having a core and a cladding.

e. transversally coupling each of the wavelength components of the encoded light signal out of the primary waveguide at different output positions along the light-guiding axis, each of these output positions being coupled to one of the stimulation sites.

This may be accomplished by placing appropriate outcoupling elements at the outcoupling end of the waveguide. In one embodiment, at least one blazed optical grating is provided in the optical fiber, an example of which may be a single chirped Bragg grating having a period selected to reflect each of the wavelength components at one of the output positions along the light-guiding axis, a plurality of uniform Bragg gratings each positioned at one of these output positions and associated with one of the wavelength components, or a long-period grating having a period selected to reflect each of the wavelength components at one of these output positions. In another embodiment, a plurality of dielectric reflectors may be provided in the optical fiber oriented at an angle with respect to the light-guiding axis, each being positioned at one of the output positions and being associated with one of the wavelength components.

An optional additional step of converting the wavelength components into electrical stimulation signals may also be provided. This step preferably includes providing a plurality of electrodes, each associated with one of the output positions. Each electrode is preferably made of a layer of photoelectric material deposited on an outer surface of the primary waveguide, in which case a polarization voltage is applied to this photoelectric material.

Alternatively, the transversal coupling of step (e) may be accomplished through an optical window provided in the primary waveguide at each of said output positions.

As mentioned above, the teachings of the present invention may be used to provide stimulation information to a variety of stimulation sites, depending on the particularities of the applications considered. For example, the proposed invention could beneficially be used as biofeedback implants in people with limb prostheses. A major problem with the use of these prostheses is the lack of feedback, or sensation. With sensors placed on the prosthesis and the proposed invention device implanted on sensitive nerves linked to the touch, one would be able to obtain sensation about the pressure, temperature, texture, weight, and position of objects touched by the prosthesis. Position and tension sensors could also be used to sense the position of the prosthesis in space and the strength applied to the motors used to activate it.

New prosthesis developments use metals, such as titanium rods, permanently and directly implanted inside the bones to which the prosthesis can be solidly attached. One can think of possibly inserting the proposed device in the body through these rods, using these rods as housing and connecting means for the device—the device being housed in the rods and the device output positions linked via the implanted electrodes to nerves. Biofeedback signals from the prosthesis sensors could then be easily sent to the central nervous system through this new link.

Based on these biofeedback possibilities, one can extrapolate and imagine the creation of new sensory input through the use of new interpretation schemas of current nervous system inputs to the brain. For example, a capacitive sensor linked with the proposed invention, implanted in the body to stimulate nerves related to pressure sensation, may provide a sensation of the density of an object—following some training to establish the new interpretation schema in the brain. This type of new sense evolution is already commercially available: the vOICe system, developed for blind people, encodes visual imagery information captured by camera into sound information via frequency and pitch. The sounds are fed to the ear of a blind patient using an earphone and, with some training, the patient's brain learns to interpret the sound information as visual information of the image captured by the camera.

Another field of application is in neurology where the proposed invention could be used to stimulate neuronal cells in live nerve tissue. This could allow communication with specific nerve cells or groups of nerve cells providing a better understanding of their interactions within the network and of the network itself. From the high density of stimulation sites achievable with the proposed invention, one can conceive the possibility of constructing an artificial spinal cord to connect members whose natural link has been severed following major injury.

Numerous modifications could be made to any of the embodiments above without departing from the scope of the present invention as defined in the appended claims.

The invention claimed is:

1. A stimulation device for transmitting stimulation information to a plurality of physiological stimulation sites in a body of a patient, said device comprising:
   light generating means for generating light having a plurality of wavelength components;
   encoding means for separately encoding at least a portion of said stimulation information into each of said wavelength components;
   a multiplexing arrangement for multiplexing said wavelength components encoded by the encoding means into an encoded light signal;
   a primary waveguide having an input end operationally connected to the multiplexing arrangement for receiving the encoded light signal therefrom, a light-guiding axis for guiding said encoded light signal therealong and an output end adapted to be implanted in the body of the patient proximate said stimulation sites, said output end having a plurality of output positions spatially distributed along said light guiding axis; and
   an outcoupling arrangement provided at said output end of the primary waveguide, said outcoupling arrangement being wavelength-sensitive for transversally coupling each of the wavelength components of the encoded light signal out of said primary waveguide at a different one of said output positions, each of said output positions to associated with one of said stimulation sites, said outcoupling arrangement transmitting the at least a portion of said stimulation information encoded in each wavelength component to the corresponding stimulation site through the associated output position.

2. A stimulation device according to claim 1, wherein said light generating means comprise at least one light-emitting diode.

3. A stimulation device according to claim 1, wherein said light generating means comprise at least one laser diode.

4. A stimulation device according to claim 1, wherein said light generating means comprise a plurality of light sources, each generating one of said wavelength components.

5. A stimulation device according to claim 4, wherein said encoding means comprise amplitude modulation controls coupled to each of said light sources for modulating an amplitude of the corresponding wavelength component generated thereby.

6. A stimulation device according to claim 5, wherein said multiplexing arrangement comprises at least one focussing element downstream said light generating means for multiplexing said wavelength components into said encoded light signal.

7. A stimulation device according to claim 1, wherein said light generating means comprise a light source generating a multi-wavelength light signal comprising said wavelength components.

8. A stimulation device according to claim 7, wherein said light generating means comprise a collimating assembly for collimating said multi-wavelength light signal.

9. A stimulation device according to claim 7, wherein said encoding means comprise:
at least one dispersing element for spatially separating said multi-wavelength light signal into said wavelength components; and
a spatial light modulator downstream said dispersive element for separately modulating an amplitude of each of said wavelength components.

10. A device according to claim 9, wherein said dispersing element is a blazed grating used in reflective mode.

11. A stimulation device according to claim 9, wherein said multiplexing arrangement comprises at least one focussing element downstream said spatial light modulator for multiplexing said wavelength components into said encoded light signal.

12. A stimulation device according to claim 11, wherein said at least one focussing element is a reflector.

13. A stimulation device according to claim 11, wherein said at least one focussing element is a refractor.

14. A stimulation device according to claim 1, wherein said primary waveguide is an optical fiber having a core and a cladding.

15. A stimulation device according to claim 14, wherein said optical fiber is a micro-structured fiber comprising a plurality of air gaps in said cladding extending along a length of said core.

16. A stimulation device according to claim 1, wherein said outcoupling arrangement comprises at least one reflecting element.

17. A stimulation device according to claim 16, wherein said at least one reflecting element comprises at least one blazed optical grating.

18. A stimulation device according to claim 17, wherein at least one blazed optical grating comprises a single chirped Bragg grating having a period selected to reflect each of said wavelength components at one of said output positions along the light-guiding axis.

19. A stimulation device according to claim 17, wherein said at least one blazed optical grating comprises a plurality of uniform Bragg gratings each positioned at one of said output positions along the light guiding axis, each of said uniform Bragg gratings being associated with one of said wavelength components.

20. A stimulation device according to claim 17, wherein said at least one blazed optical grating comprises a long-period grating having a period selected to reflect each of said wavelength components at one of said output positions along the light-guiding axis.

21. A stimulation device according to claim 1, wherein said outcoupling arrangement comprises a plurality of dielectric reflectors oriented at an angle with respect to said light-guiding axis, each of said dielectric reflectors being positioned at one of said output positions along the light guiding axis and being associated with one of said wavelength components.

22. A stimulation device according to claim 1, wherein said outcoupling arrangement comprises a plurality of transversal inserts, each associated with one of said output positions, each of said inserts reflecting one of said wavelength components out of said primary waveguide.

23. A stimulation device according to claim 1, wherein said outcoupling arrangement comprises a plurality of transversal inserts, each associated with one of said output positions, each of said inserts refracting one of said wavelength components out of said primary waveguide.

24. A stimulation device according to claim 1, further comprising a plurality of electrodes, each associated with one of said output positions, for transducing a corresponding one of said wavelength components into an electrical stimulation signal.

25. A stimulation device according to claim 24, further comprising a plurality of grooves in an outer surface of said primary waveguide for each of said output positions, each of said electrodes being received into one of said grooves.

26. A stimulation device according to claim 24, wherein each of said electrodes comprises a localised layer of photoelectric material.

27. A stimulation device according to claim 26, wherein each of said electrodes comprises a layer of biocompatible material coating said layer of photoelectric material.

28. A stimulation device according to claim 26, wherein said photoelectric material of said electrode is a photovoltaic material.

29. A stimulation device according to claim 26, wherein said photoelectric material of said electrode is a photoconductive material.

30. A stimulation device according to claim 26, further comprising voltage means for applying a polarization voltage to said photoelectric material.

31. A stimulation device according to claim 30, wherein said voltage means comprise an electrical wire extending along said primary waveguide.

32. A stimulation device according to claim 31, further comprising a groove along an outer surface of said waveguide for receiving said electrical wire.

33. A stimulation device according to claim 30, wherein said voltage means comprise an electrically conductive cladding provided along said primary waveguide.

34. A stimulation device according to claim 1, further comprising an optical window provided in said primary waveguide at each of said output positions.

35. A stimulation device according to claim 34, wherein each of said optical windows is made of a material having a refractive index higher than a refractive index along said light-guiding axis of said primary waveguide.

36. A stimulation device according to claim 34, wherein each of said optical windows is made of a dielectric material having a tailored spectral transmission profile.

37. A stimulation device according to claim 1, further comprising a plurality of secondary optical fibers, each of said secondary optical fibers having an input end coupled to one of said output positions for receiving the corresponding wavelength component therefrom, and an output end coupled to a corresponding stimulation site.

38. A stimulation device according to claim 37, wherein each of said secondary optical fiber comprises an electrode at said output end thereof for transducing a corresponding one of said wavelength components into an electrical stimulation signal.

39. A method for transmitting stimulation information to a plurality of physiological stimulation sites in a body of a patient, said method comprising the steps of:
   a. generating light having a plurality of wavelength components;
   b. separately encoding at least a portion of said stimulation information into each of said wavelength components;
   c. multiplexing said wavelength components encoded by the encoding means into an encoded light signal;
   d. guiding said encoded light signal along a light-guiding axis of a primary waveguide having an output end implanted in the body of the patient proximate said stimulation sites, said output end having a plurality of output positions spatially distributed along said light-guiding axis; and
   e. transversally coupling each of the wavelength components of the encoded light signal out of said primary waveguide at a different one of said output positions through a wavelength-sensitive outcoupling arrangement, each of said output positions being associated with one of said stimulation sites, the at least a portion of said stimulation information encoded in each wavelength component being transmitted to the corresponding stimulation site through the associated output position.

40. A method according to claim 39, wherein the generating of step (a) comprises activating a plurality of light sources, each generating one of said wavelength components.

41. A method according to claim 40, wherein the encoding of step (b) comprises controlling each of said light sources to modulate an amplitude of the wavelength component generated thereby.

42. A method according to claim 41, wherein the encoding of step (b) further comprises timing said controlling of each of the light sources to temporally modulate the wavelength component generated thereby such that said wavelength components are coupled out of said primary waveguide simultaneously.

43. A method according to claim 41, wherein the encoding of step (b) further comprises timing said controlling of each of the light sources to temporally modulate the wavelength component generated thereby such that said wavelength components are coupled out of said primary waveguide sequentially.

44. A method according to claim 39, wherein the generating of step (a) comprises activating a light source generating a multi-wavelength light signal comprising said wavelength components.

45. A method according to claim 44, comprising a step between steps (a) and (b) of separating said multi-wavelength light signal into said wavelength components.

46. A method according to claim 45, wherein the encoding of step (b) comprises modulating an amplitude of each of said wavelength components.

47. A method according to claim 39, wherein the multiplexing of step (c) comprises placing a focussing element in a path of said wavelength components.

48. A method according to claim 39, wherein the guiding of step d) comprises using an optical fiber having a core and a cladding as said primary waveguide.

49. A method according to claim 48, wherein the transversal coupling of step (e) comprises providing at least one blazed optical grating in said optical fiber.

50. A method according to claim 49, wherein said at least one blazed optical grating comprises a single chirped Bragg grating having a period selected to reflect each of said wavelength components at one of said output positions along the light-guiding axis.

51. A method according to claim 49, wherein said at least one blazed optical grating comprises a plurality of uniform Bragg gratings each positioned at one of said output positions along the light guiding axis, each of said uniform Bragg gratings being associated with one of said wavelength components.

52. A method according to claim 49, wherein said at least one blazed optical grating comprises a long-period grating having a period selected to reflect each of said wavelength components at one of said output positions along the light-guiding axis.

53. A method according to claim 48, wherein the transversal coupling of step (e) comprises providing a plurality of dielectric reflectors in said optical fiber oriented at an angle with respect to said light-guiding axis, each of said dielectric reflectors being positioned at one of said output positions along the light guiding axis and being associated with one of said wavelength components.

54. A method according to claim 39, further comprising an additional step of:
   (f) converting said wavelength components into electrical stimulation signals.

55. A method according to claim 54, wherein the converting of step (f) comprises providing a plurality of electrodes each associated with one of said output positions.

56. A method according to claim 55, wherein each of said electrodes comprises a layer of photoelectric material deposited on an outer surface of said primary waveguide.

57. A method according to claim 55, wherein step (f) further comprises applying a polarization voltage to said photoelectric material.

58. A method according to claim 39, wherein the transversal coupling of step (e) further comprises outputting each of said wavelength components through an optical window provided in said primary waveguide at each of said output positions.

59. A method according to claim 39, wherein said stimulation sites are cerebral neuronal sites along a visual pathway, said stimulation information thereby stimulating a visual response.

60. A method according to claim 39, wherein said stimulation sites are muscle tissue sites whose contraction is to be stimulated.

61. A method according to claim 39, wherein said stimulation sites host tissue whose growth is to be stimulated.

62. A method according to claim 39, wherein said stimulation sites comprise biochemical compounds adapted for photoactivation by said wavelength components.

63. A cochlear implant for transmitting auditory stimulation information to auditory neuron sites of the cochlea in situ of a patient, said cochlear implant comprising:
   light generating means for generating light having a plurality of wavelength components;
   encoding means for separately encoding at least a portion of said auditory stimulation information into each of said wavelength components;
   a multiplexing arrangement for multiplexing said wavelength components encoded by the encoding means into an encoded light signal;

a primary waveguide having an input end operationally connected to the multiplexing arrangement for receiving the encoded light signal therefrom, a light-guiding axis for guiding said encoded light signal therealong and an output end adapted to be implanted proximate said auditory neuron sites of the cochlea, said output end having a plurality of output positions spatially distributed along said light-guiding axis; and an outcoupling arrangement provided at said output end of the primary waveguide, said outcoupling arrangement being wavelength-sensitive for transversally coupling each of the wavelength components of the encoded light signal out of said primary waveguide at a respective one of a plurality of output positions along the light-guiding axis, each of said output positions being associated with a corresponding different one of said auditory neuron sites of the cochlea, said outcoupling arrangement transmitting the at least a portion of said stimulation information encoded in each wavelength component to the corresponding neuron site through the associated output position.

64. A cochlear implant according to claim 63, further comprising a plurality of electrodes, each associated with one of said output positions, for transducing a corresponding one of said wavelength components into an electrical stimulation signal.

65. A cochlear implant according to claim 63, further comprising an optical window provided in said primary waveguide at each of said output positions.

* * * * *